United States Patent
Faghihi et al.

(10) Patent No.: US 10,214,745 B2
(45) Date of Patent: Feb. 26, 2019

(54) TREATMENT OF BRAIN DERIVED NEUROTROPHIC FACTOR (BDNF) RELATED DISEASES BY INHIBITION OF NATURAL ANTISENSE TRANSCRIPT TO BDNF

(71) Applicants: The Scripps Research Institute, La Jolla, CA (US); Curna, Inc., Miami, FL (US)

(72) Inventors: Mohammad Ali Faghihi, Miami, FL (US); Carlos Coito, West Palm Beach, FL (US)

(73) Assignees: The Scripps Research Institute, La Jolla, CA (US); Curna, Inc., Miami, FL (US)

( * ) Notice: Subject to any disclaimer, the term of this patent is extended or adjusted under 35 U.S.C. 154(b) by 0 days.

(21) Appl. No.: 15/398,630

(22) Filed: Jan. 4, 2017

(65) Prior Publication Data

US 2017/0211071 A1 Jul. 27, 2017

Related U.S. Application Data

(63) Continuation of application No. 14/384,659, filed as application No. PCT/US2013/030589 on Mar. 12, 2013, now abandoned.

(60) Provisional application No. 61/614,664, filed on Mar. 23, 2012, provisional application No. 61/611,225, filed on Mar. 15, 2012.

(51) Int. Cl.
*A61K 48/00* (2006.01)
*C12N 15/113* (2010.01)

(52) U.S. Cl.
CPC ........ *C12N 15/1136* (2013.01); *C12N 15/113* (2013.01); *C12N 2310/11* (2013.01); *C12N 2310/113* (2013.01); *C12N 2310/14* (2013.01); *C12N 2310/315* (2013.01); *C12N 2310/321* (2013.01); *C12N 2310/3231* (2013.01); *C12N 2310/341* (2013.01); *C12N 2310/3521* (2013.01)

(58) Field of Classification Search
CPC ..................................................... A61K 48/00
See application file for complete search history.

(56) References Cited

U.S. PATENT DOCUMENTS

| | | |
|---|---|---|
| 3,687,808 A | 8/1972 | Thomas, Jr. et al. |
| 4,469,863 A | 9/1984 | Ts'o et al. |
| 4,476,301 A | 10/1984 | Imbach et al. |
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 4,828,979 A | 5/1989 | Klevan et al. |
| 4,845,205 A | 7/1989 | Huynh et al. |
| 4,948,882 A | 8/1990 | Ruth |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,256,775 A | 10/1993 | Froehler |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,288,512 A | 2/1994 | Seiden |
| 5,288,514 A | 2/1994 | Ellman |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,474,796 A | 12/1995 | Brennan |
| 5,476,925 A | 12/1995 | Letsinger et al. |

(Continued)

FOREIGN PATENT DOCUMENTS

| | | |
|---|---|---|
| CA | 2686933 A1 | 10/2008 |
| CN | 104583405 A | 4/2015 |

(Continued)

OTHER PUBLICATIONS

Tanila, H, (Neurobiology of Disease 97 (2017) 114-118).*

(Continued)

*Primary Examiner* — Kimberly Chong
(74) *Attorney, Agent, or Firm* — Wilson Sonsini Goodrich & Rosati

(57) ABSTRACT

The present invention relates to antisense oligonucleotides that modulate the expression of and/or function of Brain derived neurotrophic factor (BDNF), in particular, by targeting natural antisense polynucleotides of Brain derived neurotrophic factor (BDNF). The invention also relates to the identification of these antisense oligonucleotides and their use in treating diseases and disorders associated with the expression of BDNF.

23 Claims, 8 Drawing Sheets

Specification includes a Sequence Listing.

(56) References Cited

U.S. PATENT DOCUMENTS

| | | |
|---|---|---|
| 5,484,908 A | 1/1996 | Froehler et al. |
| 5,489,677 A | 2/1996 | Sanghvi et al. |
| 5,491,084 A | 2/1996 | Chalfie et al. |
| 5,491,133 A | 2/1996 | Walder et al. |
| 5,502,177 A | 3/1996 | Matteucci et al. |
| 5,506,337 A | 4/1996 | Summerton et al. |
| 5,514,785 A | 5/1996 | Van et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,525,735 A | 6/1996 | Gallop et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,549,974 A | 8/1996 | Holmes |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,567,811 A | 10/1996 | Misiura et al. |
| 5,569,588 A | 10/1996 | Ashby et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,593,853 A | 1/1997 | Chen et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De et al. |
| 5,605,662 A | 2/1997 | Heller et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,750,692 A | 5/1998 | Cook et al. |
| 5,998,148 A | 12/1999 | Bennett et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramasamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Wang et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby et al. |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tanguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Swayze et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |

(56) References Cited

U.S. PATENT DOCUMENTS

| | | |
|---|---|---|
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bumcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Swayze et al. |
| 7,745,609 B2 | 6/2010 | Bennett et al. |
| 7,749,978 B2 | 7/2010 | Sah et al. |
| 8,288,354 B2 | 10/2012 | Wahlestedt |
| 8,557,960 B2 | 10/2013 | Kim et al. |
| 8,815,808 B2 | 8/2014 | Nykjaer et al. |
| 9,074,210 B2 | 7/2015 | Collard et al. |
| 2003/0139359 A1 | 7/2003 | Dobie |
| 2003/0186920 A1 | 10/2003 | Sirois |
| 2003/0190635 A1 | 10/2003 | McSwiggen |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0132680 A1 | 7/2004 | Wong et al. |
| 2004/0137423 A1 | 7/2004 | Hayden et al. |
| 2004/0138156 A1 | 7/2004 | Schneider et al. |
| 2004/0175803 A1 | 9/2004 | Meritet et al. |
| 2004/0180336 A1 | 9/2004 | Gilad et al. |
| 2004/0248231 A1 | 12/2004 | Cordell et al. |
| 2004/0254137 A1 | 12/2004 | Ackermann et al. |
| 2004/0259247 A1 | 12/2004 | Tuschl et al. |
| 2005/0009771 A1 | 1/2005 | Levanon et al. |
| 2005/0026160 A1 | 2/2005 | Allerson et al. |
| 2005/0048641 A1 | 3/2005 | Hildebrand et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0209179 A1 | 9/2005 | McSwiggen et al. |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner et al. |
| 2007/0213274 A1 | 9/2007 | Salonen |
| 2007/0213292 A1 | 9/2007 | Stoffel et al. |
| 2007/0248590 A1 | 10/2007 | Milne et al. |
| 2008/0146788 A1 | 6/2008 | Bhat et al. |
| 2008/0168574 A1 | 7/2008 | Barry et al. |
| 2008/0221051 A1 | 9/2008 | Becker et al. |
| 2008/0234197 A1 | 9/2008 | Allam et al. |
| 2008/0293142 A1 | 11/2008 | Liu et al. |
| 2009/0110661 A1 | 4/2009 | Musatov |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0214637 A1 | 8/2009 | Musatov |
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |
| 2011/0274718 A1 | 11/2011 | During et al. |
| 2011/0288160 A1 | 11/2011 | During et al. |
| 2011/0319475 A1 | 12/2011 | Collard et al. |
| 2012/0208747 A1 | 8/2012 | Kim et al. |
| 2015/0031750 A1 | 1/2015 | Faghihi et al. |

FOREIGN PATENT DOCUMENTS

| | | |
|---|---|---|
| EP | 0335451 A2 | 10/1989 |
| EP | 0335451 A3 | 10/1989 |
| EP | 0910399 B1 | 9/2002 |
| EP | 2825648 A2 | 1/2015 |
| EP | 2396038 B1 | 10/2015 |
| WO | WO-8403564 A1 | 9/1984 |
| WO | WO-9119735 A1 | 12/1991 |
| WO | WO-9200091 A1 | 1/1992 |
| WO | WO-9208796 A1 | 5/1992 |
| WO | WO-9320242 A1 | 10/1993 |
| WO | WO-9426887 A1 | 11/1994 |
| WO | WO-9428143 A1 | 12/1994 |
| WO | WO-9515373 A2 | 6/1995 |
| WO | WO-9522618 A1 | 8/1995 |
| WO | WO-9525116 A1 | 9/1995 |
| WO | WO-9535505 A1 | 12/1995 |
| WO | WO-9627663 A2 | 9/1996 |
| WO | WO-9739120 A2 | 10/1997 |
| WO | WO-9745135 A1 | 12/1997 |
| WO | WO-9914226 A2 | 3/1999 |
| WO | WO-9939352 A1 | 8/1999 |
| WO | WO-0057837 A2 | 10/2000 |
| WO | WO-0061770 A2 | 10/2000 |
| WO | WO-0100669 A2 | 1/2001 |
| WO | WO-0121631 A2 | 3/2001 |
| WO | WO-0125488 A2 | 4/2001 |
| WO | WO-0151630 A1 | 7/2001 |
| WO | WO-02062840 A1 | 8/2002 |
| WO | WO-02068688 A1 | 9/2002 |
| WO | WO-02085308 A2 | 10/2002 |
| WO | WO-2004016255 A1 | 2/2004 |
| WO | WO-2004024079 A2 | 3/2004 |
| WO | WO-2004030750 A1 | 4/2004 |
| WO | WO-2004041838 A1 | 5/2004 |
| WO | WO-2004104161 A2 | 12/2004 |
| WO | WO-2005045034 A2 | 5/2005 |
| WO | WO-2005070136 A2 | 8/2005 |
| WO | WO-2005091862 A1 | 9/2005 |
| WO | WO-2007028065 A2 | 3/2007 |
| WO | WO-2007071182 A1 | 6/2007 |
| WO | WO-2007087113 A2 | 8/2007 |
| WO | WO-2007138023 A1 | 12/2007 |
| WO | WO-2008057556 A2 | 5/2008 |
| WO | WO-2008066672 A2 | 6/2008 |
| WO | WO-2008087561 A2 | 7/2008 |
| WO | WO-2009058970 A2 | 5/2009 |
| WO | WO-2010002984 A1 | 1/2010 |
| WO | WO-2010040571 A2 | 4/2010 |
| WO | WO-2010054364 A1 | 5/2010 |
| WO | WO-2010058227 A2 | 5/2010 |
| WO | WO-2010093904 A2 | 8/2010 |
| WO | WO-2012068340 A2 | 5/2012 |
| WO | WO-2013138374 A2 | 9/2013 |

OTHER PUBLICATIONS

Chinese Patent Application No. 2013800248744 Second Office Action dated Dec. 20, 2016.
European Patent Application No. 13712635.5 Communication dated Jan. 19, 2017.
Japanese Patent Application No. 2015-500527 Office Action dated Dec. 19, 2016.
Varela et al., Natural antisense makes sense for gene-specific activation in brain. Molecular Therapy-Nucleic Acids, 1:e24, 4 pages, 2012.
Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).

(56) References Cited

OTHER PUBLICATIONS

Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).
Bernstein, E., et al., "Role for a bidentate ribonuclease in the initiation step of RNA interference," Nature 409:363-366 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1989).
Campbell, et al., "Phosphonate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS 98(17):9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Cech, T., "Ribozymes and Their Medical Implications," American. Med Assoc. 260:3030-3035 (1988).
Celts, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol. 6:632-639 (1995).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Chen, et al., "Expression of ssDNA in Mammalian Cells," BioTechniques 34:167-171 (2003).
Cheng, J. et al., "Transcriptional maps of 10 human chromosomes at 5-nucleotide resolution," Science 308:5725:1149-1154 (2005).
Chinese Patent Application No. 201380024874.4 First Office Action dated Feb. 2, 2016.
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).

Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng, et al., "Small interfering RNA targeting the PINK I induces apoptosis in dopaminergic cells SH-SY5Y" Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoom, et al., "Determinants of specific RNA interference-mediated silencing of human β-globin alleles differing by a single nucleotide polymorphism." PNAS, 103:15, 5953-5958 (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Englisch et al., 'Angewandle Chemie, International Edition', #613, p. A-115 (1991).
Espeseth, et al., A genome wide analysis of ubiquitin ligases in APP processing identifies a novel regulator of BACE1 mRNA levels, Mol. Cell Neurosci. 33: 227-235 (2006).
European Patent Application No. 13712635.5 Communication dated Jan. 13, 2016.
Faghihi et al., "Evidence for natural antisense transcript-mediated inhibition of microRNA function," Genome Biology 2010, 11:R56, 13 pgs.
Faghihi et al., "Expression of a noncoding RNA is elevated in Alzheimer's disease and drives rapid feed-forward regulation of B-secretase expression," Nat. Med. Jul. 2008: 14(7):723-730.
Faghihi, M. & Wahlestedt, C., "RNA interference is not involved in natural antisense mediated regulation of gene expression in mammals," Genome Biol, 6 pages (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Genbank Accession NM 000559.2. "*Homo sapiens* hemoglobin, gamma A (HBG1), mRNA." Jan. 26, 2014. 2 pages.
Giuliano, et al., "Determination of Intracellular pH of BALB/c-3T3 Cells Using the Fluorescence of Pyranine," Anal. Biochem 167:362-371 (1987).
Giuliano, et al., "Fluorescent Protein Biosensors: Measurement of Molecular Dynamics in Living Cells," Ann. Rev. of Biophysics and Biomolecular Structure 24:405-434 (1995).

(56) References Cited

OTHER PUBLICATIONS

Giuliano, et al., "Light-Optical-Based Reagents for the Measurement and Manipulation of Ions, Metabolites, and Macromolecules in Living Cells," Methods in Neuroscience 27:1-16 (1995).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker and Proudfoot, "Dicer-Dependent turnover of intergenic transcripts from the human β-globin gene cluster." Molecular and Cellular Biology, 25:21, 9724-9733 (2005).
Heller, et al., "Discovery and analysis of inflammatory disease-related genes using cDNA microarrays," PNAS U.S.A. 94:2150-2155 (1997).
Herdewin P., "Heterocyclic Modifications of Oligonucleotides and Antisense Technology," Antisense & Nucleic Acid Drug Dev., 10:297-310 (2000).
Hirschmann, et al. Nonpeptidal Peptidomimetics with β-D-Glucose Scaffolding. A Partial Somatostatin Agonist Bearing a Close Structural Relationship to a Potent, Selective Substance P Antagonist. J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
Single gene variation linked to obesity: Variation in the BDNF gene may affect brain's regulation of appetite, study suggests. Science Daily, published Oct. 29, 2015, 7 pages. http://www.sciencedaily.com/releases/2015/10/151029141133.htm.
International Human Genome Sequencing Consortium "Finishing the euchromatic sequence of the human genome." Nature 431:7011:931-945 (2004).
International Preliminary Report on Patentability dated Sep. 25, 2014 for PCT/US2013/030589.
International Search Report and Written Opinion dated Oct. 28, 2013 for PCT/US2013/030589.
International Search Report dated Sep. 29, 2008 for PCT/US2006/062672.
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kocerha, et al., "microRNAs in CNS disorders," Neuromolecular Med. 2009; 11(3):162-72.
Kornberg, A., DNA Replication, W.H. Freeman & Co., San Francisco, 1980 (1992?) pp. 75-77.
Kraynack, et al. Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Le Gal La Salle et al., "An Adenovirus Vector for Gene Transfer into Neurons and Glia in the Brain," Science 259:988-990 (1993).
Lebl, et al., "One-bead-one-structure combinatorial libraries," Biopolymers 37:177-198 (1995).
Letsinger et al. Cholesteryl-conjugated oligonucleotides: Synthesis, properties, and activity as inhibitors of replication of human immunodeficiency virus in cell culture. PNAS 86:6553-6556 (1989).
Li et al., "Control of APP processing and Aβ generation level by BACE1 enzymatic activity and transcription," Faseb J 20; 285-292 (2006).
Li, et al., Increased plaque burden in brains of APP mutant MnSOD heterozygous knockout mice. J. Neurochem 89 1308-1312 (2004a).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Magistri et al., "Regulation of chromatin structure by long noncoding RNAs: focus on natural antisense transcripts." Trends in Genetics, 28:8, 389-396, 2012.
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Manoharan, M., "2'-Carbohydrate modifications in antisense oligonucleotide therapy: importance of conformation, configuration and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Modarresi et al., "Inhibition of natural antisense transcripts in vivo results in gene-specific transcriptional upregulation." Nature Biotechnology. 30:5, p. 453-459, 2012.
Modarresi et al., "Knockdown of BACE1-AS Nonprotein-Coding Transcript Modulates Beta-Amyloid Related Hippocampal Neurogenesis," International Journ. Of Alzeheimers, vol. 2011, Article ID 929042, 11 pgs.
Morelli et al., "The antisense bcl-2-IgH transcript is an optimal target for synthetic oligonucleotides," PNAS USA 94:8150-8155 (1997).

(56) References Cited

OTHER PUBLICATIONS

Mou et al., Human obesity associated with an intronic SNP in the brain-derived neurotropic factor locus. Cell Reports, 13:1-8 (2015) http://dx.doi.org/10.1016/j.ceirep.2015.09.065.
Nielsen, et al., "Sequence-Selective Recognition of DNA by Strand Displacement with a Thymine-Substituted Polyamide," Science 254:1497-1500 (1991).
Oberhauser et al. Effective incorporation of 2'-O-methyl-oligoribonucleotides into liposomes and enhanced cell association through modification with thiocholesterol. Nucl. Acids Res. 20:533-538 (1992).
Orgel, Selection in vitro. Proc. R. Soc. London, B 205, 435-442 (1979).
Petit, et al., "Wild-type PINK1 prevents basal and induced neuronal apoptsis, a protective effect abrogated by Parkinson disease-related mutations," Journ. Biol. Chem. vol. 280, No. 40, pp. 34025-34032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Pruunsild et al., "Dissecting the human BDNF locus: Bidirectional transcription, complex splicing, and multiple promotors." Genomics, Academic Press, San Diego, CA, 90:3, 397-406 (2007).
Quantin, et al., "Adenovirus as an expression vector in muscle cells in vivo," PNAS 89:2581-2584 (1992).
Robb, et al. Post-transcriptional regulation of endothelial nitric-oxide synthase by an overlapping antisense mRNA transcript. J Biol Chem. Sep. 3, 2004;279(36):37982-96. Epub Jul. 2, 2004.
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Russian Patent Application No. 2014140112 Office Action dated Oct. 24, 2016.
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele, et al., "The human PINK1 locus is regulated in vivo by a non-coding natural antisense RNA during modulation of mitochondrial function," BMC Genomics, vol. 8, No. 1, p. 74 (2007).
Schena, et al., "Parallel human genome analysis: Microarray-based expression monitoring of 1000 genes," PNAS 93:10614-10619(1996).
Shea et al. Synthesis, hybridization properties and antiviral activity of lipid-oligodeoxynucleotide conjugates. Nucl. Acids Res 18:3777-3783 (1990).
Shen et al., "Modification of globin gene expression by RNA targeting strategies." Experimental Hematology, vol. 35, 1209-1218 (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Smith and Waterman, Comparison of Biosequences. Adv. Appl. Math., 2:482-489 (1981).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun et al., "Downregulation of Sirt1 by antisense oligonucleotides induces apoptosis and enhances radiation sensitization in A549 lung cancer cells." Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk et al. Inhibition of HIV proliferation in MT-4 cells by antisense oligonucleotide conjugated to lipophilic groups. Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, KY, "Identification of Differential Gene Expression by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Uhlenbeck, O. C., A small catalytic oligoribonucleotide. Nature, 328: 596-600 (1987).
Ulhman, E., "Recent advances in the medical chemistry of antisense oligonucleotide," Current Opinions in Drug Discovery & Development 3:203-213 (2000).
U.S. Appl. No. 14/384,659 Office Action dated Jan. 8, 2016.
U.S. Appl. No. 12/159,607 Office Action dated Aug. 25, 2010.
U.S. Appl. No. 12/159,607 Office Action dated Jan. 27, 2012.
U.S. Appl. No. 12/159,607 Office Action dated Jan. 7, 2010.
U.S. Appl. No. 12/159,607 Office Action dated Jun. 13, 2011.
U.S. Appl. No. 13/563,581 Office Action dated Mar. 24, 2016.
U.S. Appl. No. 14/384,659 Office Action dated Jul. 7, 2016.
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, C., "Antisense oligonucleotide strategies in neuropharmacology," Trends Pharmacol Sci 15:2:42-46 (1994).
Wahlestedt, "Natural antisense and noncoding RNA transcripts as potential drug targets," Drug Discovery Today 11 (11/12):503-508 (2006).
Walsh, et al., The role of cell-derived oligomers of Aβ in Alzheimer's disease and avenues for therapeutic intervention, Biochem Soc Trans 33: 1087-1090 (2005).

(56) References Cited

OTHER PUBLICATIONS

Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-oxide Synthase Antisense (NOS3AS) Gene Encodes an Autophagy-related Protein (APG9-like2) Highly Expressed in Trophoblast," Journ. Biol. Chem. vol. 280, No. 18, pp. 18283-18290 (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
U.S. Appl. No. 14/723,740 Office Action dated Jan. 17, 2017.
Chinese Patent Application No. 201380024874.4 Office Action dated Oct. 11, 2017.
Japanese Patent Application No. 2015-500527 Decision of Rejection dated Oct. 4, 2017.
Russia Patent Application No. 2014140112 Office Action dated Nov. 29, 2017.

\* cited by examiner

Control siRNA (3d post-plating)

BDNF-AS siRNA (3d post-plating)

Control siRNA (7d post-plating)

BDNF-AS siRNA (7d post-plating)

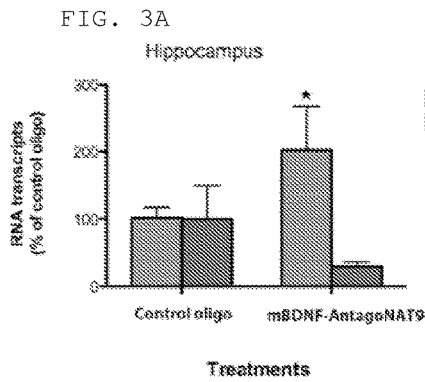
FIG. 3A Hippocampus
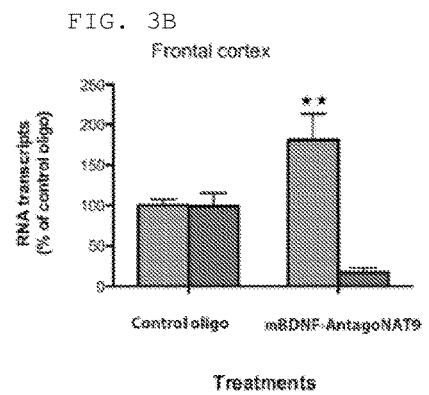
FIG. 3B Frontal cortex
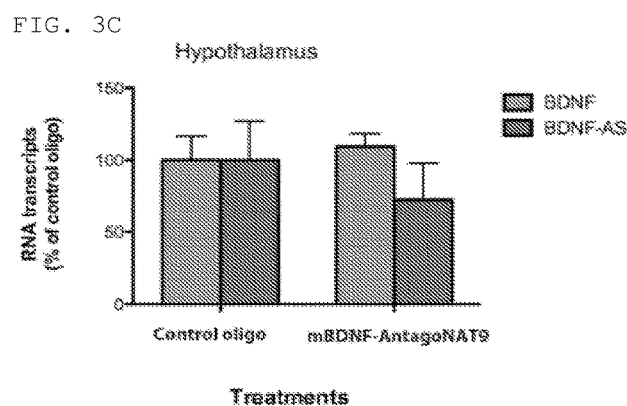
FIG. 3C Hypothalamus
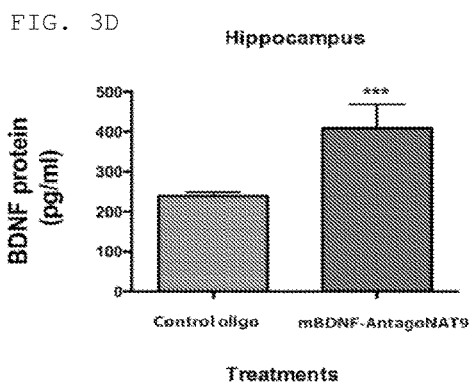
FIG. 3D Hippocampus
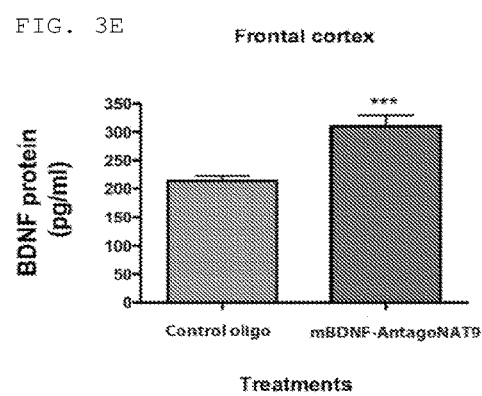
FIG. 3E Frontal cortex FIG. 4A Control oligonucleotide
FIG. 4B mBDNF-AntagoNAT9
FIG. 4C
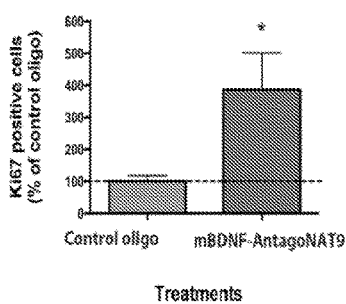
FIG. 4D
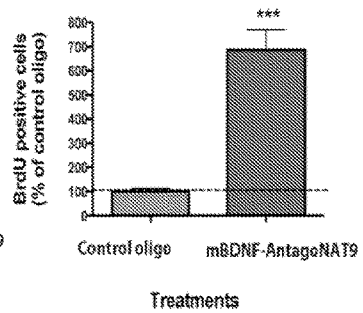
FIG. 4E
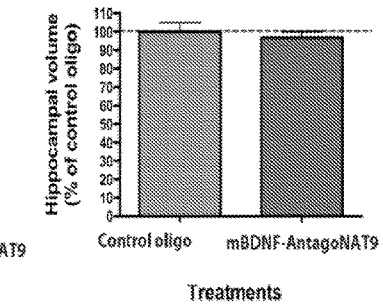

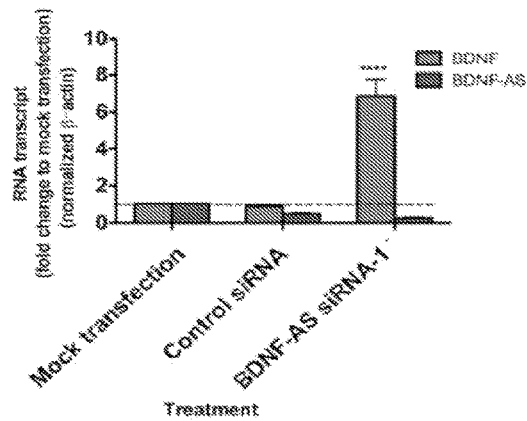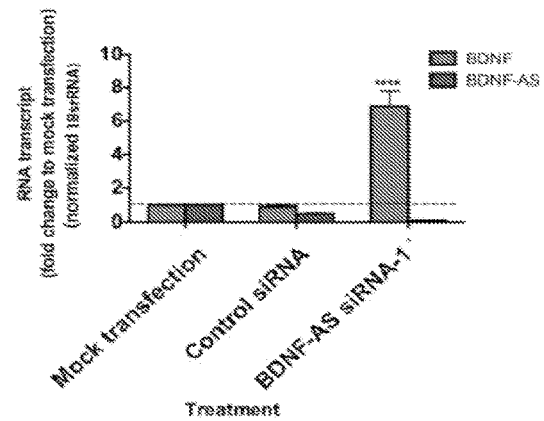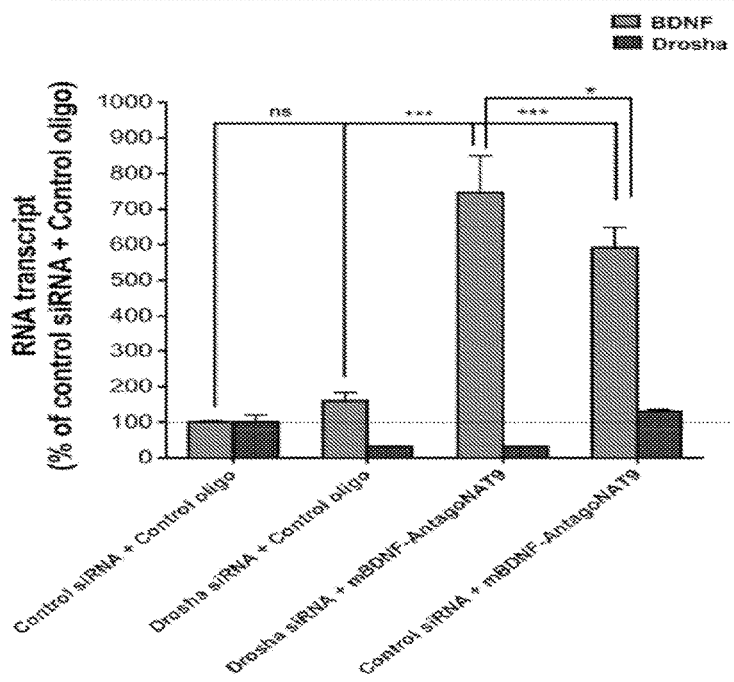

SEQUENCE LISTING

<160> NUMBER OF SEQ ID NOS: 68

<210> SEQ ID NO 1
<211> LENGTH: 4755
<212> TYPE: DNA
<213> ORGANISM: Homo sapiens

<400> SEQUENCE: 1

```
cacacacaca cacacacaca gagagaacat ctctagtaaa aagaaaagtt gagctttctt      60
agctagatgt gtgtattagc cagaaaaagc caaggagtga agggttttag agaactggag     120
gagataaagt ggagtctgca tatgggaggc atttgaaatg gacttaaatg tcttttttaat    180 gctgacttt tcagttttct ccttaccaga cacattgttt tcatgacatt agccccaggc     240
atagacacat cattaaaatg aacatgtcaa aaaatgattt ctgtttagaa ataagcaaaa     300
cattttcagt tgtgaccacc caggtgtaga ataaagaaca gtggaattgg gagccctgag     360
ttctaacata aactttcttc atgacataag gcaagtcttc tatggccttt ggtttcctta     420
cctgtaaaac aggatggctc aatgaaatta tctttcttct ttgctataat agagtatctc     480
tgtgggaaga ggaaaaaaaa agtcaattta aaggctcctt atagttcccc aactgctgtt     540
ttattgtgct attcatgcct agacatcaca tagctagaaa ggcccatcag accoctcagg     600 ccactgctgt tcctgtcaca cattcctgca aaggaccatg ttgctaactt gaaaaaaatt     660
actattaatt acacttgcag ttgttgctta gtaacattta tgattttgtg tttctcgtga     720
cagcatgagc agagatcatt aaaaattaaa cttacaaagc tgctaaagtg ggaagaagga     780
gaacttgaag ccacaatttt tgcacttgct tagaagccat ctaatctcag gttatatgct     840
agatcttggg ggcaaacact gcatgtctct ggtttatatt aaaccacata cagcacacta     900
ctgacactga tttgtgtctg gtgcagctgg agtttatcac caagacataa aaaaaccttg     960
accctgcaga atggcctgga attacaatca gatgggccac atggcatccc ggtgaaagaa    1020
agccctaacc agttttctgt cttgtttctg ctttctccct acagttccac caggtgagaa    1080
gagtgatgac catcctttc cttactatgg ttatttcata ctttggttgc atgaaggctg    1140 ccccccatgaa agaagcaaac atccgaggac aaggtggctt ggcctaccca ggtgtgcgga    1200
cccatgggac tctggagagc gtgaatgggc ccaaggcagg ttcaagaggc ttgacatcat   1260
tggctgacac tttcgaacac gtgatagaag agctgttgga tgaggaccag aaagttcggc   1320
```

```
ccaatgaaga aaacaataag gacgcagact tgtacacgtc cagggtgatg ctcagtagtc    1380
aagtgccttt ggagcctcct cttctctttc tgctggagga atacaaaaat tacctagatg    1440
ctgcaaacat gtccatgagg gtccggcgcc actctgaccc tgcccgccga ggggagctga    1500
gcgtgtgtga cagtattagt gagtgggtaa cggcggcaga caaaaagact gcagtggaca    1560
tgtcgggcgg gacggtcaca gtccttgaaa aggtccctgt atcaaaaggc caactgaagc    1620
aatacttcta cgagaccaag tgcaatccca tgggttacac aaaagaaggc tgcaggggca    1680
tagacaaaag gcattggaac tcccagtgcc gaactaccca gtcgtacgtg cgggccctta    1740
ccatggatag caaaaagaga attggctggc gattcataag gatagacact tcttgtgtat    1800
gtacattgac cattaaaagg ggaagatagt ggatttatgt tgtatagatt agattatatt    1860
gagacaaaaa ttatctattt gtatatatac ataacagggt aaattattca gttaagaaaa    1920
aaataatttt atgaactgca tgtataaatg aagtttatac agtacagtgg ttctacaatc    1980
tatttattgg acatgtccat gaccagaagg gaaacagtca tttgcgcaca acttaaaaag    2040
tctgcattac attccttgat aatgttgtgg tttgttgccg ttgccaagaa ctgaaaacat    2100
aaaaagttaa aaaaaataat aaattgcatg ctgctttaat tgtgaattga taataaactg    2160
tcctctttca gaaaacagaa aaaaacacac acacacacaa caaaaatttg aaccaaaaca    2220
ttccgtttac attttagaca gtaagtatct tcgttcttgt tagtactata tctgttttac    2280
tgcttttaac ttctgatagc gttggaatta aacaatgtc aaggtgctgt tgtcattgct    2340
ttactggctt aggggatggg ggatgggggg tatatttttg tttgttttgt gttttttttt    2400
cgtttgtttg ttttgttttt tagttcccac agggagtaga gatggggaaa gaattcctac    2460
aatatatatt ctggctgata aagatacat ttgtatgttg tgaagatgtt tgcaatatcg    2520
atcagatgac tagaaagtga ataaaaatta aggcaactga acaaaaaaat gctcacactc    2580
cacatcccgt gatgcacctc ccaggccccg ctcattcttt gggcgttggt cagagtaagc    2640
tgcttttgac ggaaggacct atgtttgctc agaacacatt cttcccccc ctccccctct    2700 ggtctcctct ttgttttgtt ttaaggaaga aaaatcagtt gcgcgttctg aaatatttta    2760
ccactgctgt gaacaagtga acacattgtg tcacatcatg acactcgtat aagcatggag    2820
aacagtgatt ttttttaga acagaaaaca acaaaaaata accccaaaat gaagattatt    2880
ttttatgagg agtgaacatt tgggtaaatc atggctaagc ttaaaaaaaa ctcatggtga    2940
ggcttaacaa tgtcttgtaa gcaaaaggta gagccctgta tcaacccaga acacctaga    3000 tcagaacagg aatccacatt gccagtgaca tgagactgaa cagccaaatg gaggctatgt    3060
ggagttggca ttgcatttac cggcagtgcg ggaggaattt ctgagtggcc atcccaaggt    3120
ctaggtggag gtggggcatg gtatttgaga cattccaaaa cgaaggcctc tgaaggaccc    3180
ttcagaggtg gctctggaat gacatgtgtc aagctgcttg gacctcgtgc tttaagtgcc    3240
tacattatct aactgtgctc aagaggttct cgactggagg accacactca agccgactta    3300
tgcccaccat cccacctctg gataatttg cataaaattg gattagcctg gagcaggttg    3360
ggagccaaat gtggcatttg tgatcatgag attgatgcaa tgagatagaa gatgtttgct    3420
acctgaacac ttattgcttt gaaactagac ttgaggaaac cagggtttat cttttgagaa    3480
cttttggtaa gggaaaaggg aacaggaaaa gaaaccccaa actcaggccg aatgatcaag    3540
gggacccata ggaaatcttg tccagagaca agacttcggg aaggtgtctg acattcaga    3600 acaccaagac ttgaaggtgc cttgctcaat ggaagaggcc aggacagagc tgacaaaatt    3660
ttgctcccca gtgaaggcca cagcaacctt ctgcccatcc tgtctgttca tggagagggt    3720
```

```
cccctgcctca cctctgccat tttgggttag gagaagtcaa gttgggagcc tgaaatagtg    3780
gttcttggaa aaatggatcc ccagtgaaaa ctagagctct aagcccattc agcccatttc    3840
acacctgaaa atgttagtga tcaccacttg gaccagcatc cttaagtatc agaaagcccc    3900
aagcaattgc tgcatcttag tagggtgagg gataagcaaa agaggatgtt caccataacc    3960
caggaatgaa gataccatca gcaaagaatt tcaatttgtt cagtctttca tttagagcta    4020
gtctttcaca gtaccatctg aatacctctt gaaagaagg aagactttac gtagtgtaga    4080
tttgttttgt gttgtttgaa atattatct ttgtaattat ttttaatatg taaggaatgc    4140
ttggaatatc tgctatatgt caactttatg cagcttcctt ttgagggaca aatttaaaac    4200
aaacaacccc ccatcacaaa cttaaaggat tgcaagggcc agatctgtta agtggtttca    4260
taggagacac atccagcaat tgtgtggtca gtggctcttt tacccaataa gatacatcac    4320
agtcacatgc ttgatggttt atgttgacct aagatttatt ttgttaaaat ctctctctgt    4380
tgtgttcgtt cttgttctgt tttgttttgt tttttaaagt cttgctgtgg tctctttgtg    4440
gcagaagtgt ttcatgcatg gcagcaggcc tgttgctttt ttatggcgat tcccattgaa    4500
aatgtaagta aatgtctgtg gccttgttct ctctatggta aagatattat tcaccatgta    4560
aaacaaaaaa caatatttat tgtattttag tatatttata taattatgtt attgaaaaaa    4620
attggcatta aaacttaacc gcatcagaac ctattgtaaa tacaagttct atttaagtgt    4680
actaattaac atataatata tgttttaaat atagaatttt taatgttttt aaatatattt    4740
tcaaagtaca taaaa                                                    4755
```

<210> SEQ ID NO 2
<211> LENGTH: 4302
<212> TYPE: DNA
<213> ORGANISM: Mus musculus
<400> SEQUENCE: 2

```
taaagcagta gccggctggt gcagaaaagc aacaagttcc ccagcggtct tcccgcccta     60
gcttgacaag gcgaagggtt tcttacctgg cgacagggaa atctcctgag ccgagctcat    120 cttttgccaga gccccaggtg tgacctgagc agtgggcaaa ggatcggcgt gcaaattgga    180 ttattttat gggggtactc tgaaactccc tcactttctc tgggaacttt tgtgctagg     240 gctcagtgac aggcgttgag aaagctgctt caggaaacgc ccgctatata gcagggcaat    300
tggacagtca ttggtaacct cgctcattca ttagaatcac gtaagaactc aaagggaaac    360
gtgtctctca gaatgagggc gtttgcgtaa atctataggt ttttcaacat cgatgccagt    420
tgctttgtct tctgtagtcg ccaaggtgga tgagagttga agctttgcgg atattgcgaa    480
gggttattag attcataagt cacaccaagt ggtgggcgat ccactgagca agccgaact    540 tctcacatga tgacttcaaa caagacacat taccttcctg catctgttgg ggagacaaga    600
ttttaagaca ctgagtctcc aggacagcaa agccacaatg ttccaccagg tgaagagt     660 gatgaccatc cttttcctta ctatggttat ttcatacttc ggttgcatga aggcggcgcc    720
catgaaagaa gtaaacgtcc acggacaagg caacttggcc tacccaggtg tgcggaccca    780
tgggactctg gagagcgtga atgggcccag ggcaggttcg agaggtctga cgacgacatc    840
actggctgac acttttgagc acgtcatcga agagctgctg gatgaggacc agaaggttcg    900
gcccaacgaa gaaaaccata aggacgcgga cttgtacact tccgggtga tgctcagcag    960 tcaagtgcct ttggagcctc ctctactctt tctgctggag gaatacaaaa attacctgga   1020
tgccgcaaac atgtctatga gggttcggcg ccactccgac cctgcccgcc gtggggagct   1080
```

```
gagcgtgtgt gacagtatta gcgagtgggt cacagcggca gataaaaaga ctgcagtgga    1140
catgtctggc gggacggtca cagtcctaga gaaagtcccg gtatccaaag gccaactgaa    1200
gcagtatttc tacgagacca agtgtaatcc catgggttac accaaggaag gctgcagggg    1260
catagacaaa aggcactgga actcgcaatg ccgaactacc caatcgtatg ttcgggccct    1320
tactatggat agcaaaaaga gaattggctg gcgattcata aggatagaca cttcctgtgt    1380
atgtacactg accattaaaa ggggaagata gtggatttat gttgtataga ttatattgag    1440
acaaaattat ctatttgtat atatacataa cagggtaaat tattcagtta agaaaaaata    1500
attttatgaa ctgcatgtat aaatgaagtt tatacagtac agtggttcta caatctattt    1560
attggacata tccatgacct gaaaggaaac agtcatttgc gcacaacttt aaaagtctgc    1620
attacattcc tcgataatgt tgtggtttgt tgccgttgcc aagaattgaa aacaaaaagt    1680
ttaaaaaaaa taataataaa ttgcatgctg ctttaattgt gaattgataa taaactgtcc    1740
ctctttcaga aaacagatta aaaaacaaaa aacaaaaaa aaaaaacaa aaacaaaaa    1800 caaaaattgg aaccaaaaca ttccgtttac attttagaca ctaagtatct tcgttcttgt    1860
tagtactctg ttttactgct ttcgacttct gatagcgttg gaattaaaac aatgtcaagg    1920
tgctgttgtc attgctttac tggcgtaagg gacggggaat ggggaggggta gatttctgtt    1980 tgttttgtgt tttattttgt ttgtttgttt gttttgtttt ttagttccac ccggagtagg    2040
gatggagaaa atttcttcac tatccattct ggttgataaa gcgttacatt tgtatgttgt    2100
aaagatgttt gcaaaatcca atcagatgac tggaaaacaa ataaaaatta aggcaactga    2160
ataaaatgct cacactccac tgcccatgat gtatctccct ggtcccccctc agctcactct    2220 tctggcatgg gtcagggaaa attgcttta ttggaaagac cagcatttgt tcaaagcata    2280
ctctttccct ccctcctccc attttggtcc cttcttttg ttttgtttta agaaagaaaa    2340
ttaagttgcg cgctttaaaa tattttacta ctgctacaaa cagatgaaca atgtgtgtca    2400
ttttatgaca ctcatggaaa acagtgattt tttttaccc taaagaaaaa caaataaaaa    2460
taacccaaaa tattctttt taaaaggca taaatattgg gtaaattgta atatggccta    2520
acagtgtttg cagataaaag ttattgtata cacccagata cttagataag agcagggatc    2580
cacactgcca ttgaaatagg actgaatggc cctgcggagg ctaagtggag ctgacatact    2640
atttcctggc agtgcaggag gaatttctga gtggccatcc taaggtctag gatgaggtg    2700 gggaatggta cttgagacat tcctaaagga aggctcggaa gcacccttca gagcaggctc    2760
tggaatgatg tgtcaagttg cttaggcctt ctgctttaag tgcctacatt acctaacagt    2820
gctcaagagg ttctcgattg gagaaccaca ctcaaatcca tttatagcct ccatcccatt    2880
tctaaataat tgtgtataaa gttggattaa cctggagcaa cttttggatcc aaatatggca    2940 cagcaataat gatattaatg cagcatgatg ggaaatgttt gctgtgaaga gaattgattt    3000
gctttgagct tagacttcag gaagcctagg ttttttattt tttttatttt gagacatttt    3060
ggtaaaagga aaaaagaaa acaaacaaac aaacaaacaa aaccagaaaa agcatcaaaa    3120
ctcaggcaga atgagcaatg tctgaaaggg ctagaaaaac aagacatagc aaggtgcttt    3180
cactgtgaaa gagacaagaa cacaggagga atattgctt cagtgaagag cacagacggc    3240
tcctgccaat ttattacaag agtcccgtct gtactttacc ctttggggtt agaagtcaag    3300
ttggaagcct gaatgaatgg acccaatgag aactagtgtt aagcccattt ccctagtcag    3360 gttttttca agcgtgaatg tgttagtggt tactctcctg ggttcctgag catcagaaaa    3420 aaaaaaaaa agaggcaaac aatcgcttca tcttaggagt ggaaaggaaa cagaagtgga    3480
```

```
cgtccgctgt gactcaggga gtgaagatac catcagcaaa tagtttcttt tttgttcatt      3540
cgttcctttc gagttagcct gtcttttgga ataccactga atatgctgtt tttgaaagac      3600
ttcatgtagc atagattgtt ttgtgccgtt taccaaatta acctttgtca tcgtttttta      3660
acctattcag gaatgcttgg aatatctgct ctatgttaac tttttgcagc ttcattctga      3720
gagacattag tcaaacaaac aaaaggatcc ccatcacaat cttacagtac tgcaagggcc      3780
aggtctgtta atcggcttca caggagacat cagcaattgt gtggtcagtg gctggctctc      3840
ttacccacta agatacatca tagctacatg ttggtggttt atgttgacct gagatttatt      3900
tgttaaaatc tcttcttcgt ttctgttcgt tctggttctg ttctgttctg ttctgttctg      3960
ttttggtttt aaagtcttgc tgtggtctct tgttggcaga aatgttttat gcatggcagc      4020
aggcctgttg ctttttttata gtgattccca ttgaaactgt aagtaaatgt ctgtggcctt      4080
gttctctcta tggtaaagat attattcacc atgtaaaaca agaaaaaata tttattgtat      4140
tttagtatat ttatataatt atgttattga aaaaattggc attaaaactt aaccacatca      4200
gaagcctatt gtaaatacag gttctattta agtgtaccaa ttaacatata atatatgttt      4260
taaatataga atttttaatg ttttttaaata tattttcaaa gt                       4302
```

<210> SEQ ID NO 3
<211> LENGTH: 1279
<212> TYPE: DNA
<213> ORGANISM: Homo sapiens

<400> SEQUENCE: 3

```
atcgcgagat caggaaggtg gccgagtgtg tcgccgcggc catcaggcac ttctccttcc        60
tgcccttgta tgaagaagga tgtgtttgct tcccttgtg ccatgattgt aaatttcctg       120
aggcctcctc agccctgcag aactggctag agcaatgtat cttaggctca cttaaggaag       180
ctgtagagat gagcccaagg agggaaacca gaagagcccc ccaggctcac cagttgtttg       240
ttggctccct acaaacatgt cattcaagtg gctaatctta caacagcaca aattcatcta       300
accagaaaga gaaggaggag ctccaaaggc acttgactac tgagcatcac cctggacgtg       360
tacaagtctg cgtccttatt gttttcttca ttgggccgaa cttctggtc ctcatccaac       420 agctcttcta tcacgtgttc gaaagtgtca gccaatgatg tcaagcctct tgaacctgcc       480
ttgggcccat tcacgctctc cagagtccca tgggtccgca cacctggaga tactctatta       540
tagcaaagaa gaaagataat tcattgagc catcctgttt tacaggattt tccctcctgg       600
tgagtcaaaa tgaacaagaa ataccccagg acctcccttc cctccttggc cattaatgag       660
atgaaggcaa ttaactcaca tagtataaat gaatcatttg aggtgatgac tgcattttag       720
gcaaatgatg actttcttgg ttccattggt ttgcaagtaa aagttacaca cattgaaaag       780
acactgaaac agatttccta aatgcttcat tttctggatg caccaatgtt gacctactat       840
acatgttaaa tggttttaaa atatcacctt aaaataaagg aaacttccag ctactaactc       900
agctctgaat gggctatgaa aggctccaaa ggtatgtgaa aaattactgt tattttgctt       960
taaaaaatgt gatgtctaag agtgtctgca atgttctaat gcttcaaaac atgtacgtaa      1020
gccttgttta tctggaaatc atttctttct gcttatatca tttataaata gaaaatgttc      1080
tgtaataact aaaatagtt ccacatacat aatgctttta gtgtcataat acttactact       1140
ggtctatatt taccaacatt tatcacattt tacaaaatga agtagaagaa aaaaagaca      1200 acgactttat ggccctggaa ttccagtaat ggtgaccaac atgtttttaaa ttccagtaaa      1260 ggttatggtt acatttcaa                                                  1279
```

<210> SEQ ID NO 4
<211> LENGTH: 1478
<212> TYPE: DNA
<213> ORGANISM: Homo sapiens

<400> SEQUENCE: 4

```
atcgcgagat caggaaggtg gccgagtgtg tcgccgcggc catcaggcac ttctccttcc      60
tgcccttgta tgaagaagga tgtgtttgct tccccttgtg ccatgattgt aaatttcctg     120
aggcctcctc agccctgcag aactggggtt atagccatgt gactgatctt cgtccaagaa     180
tatgtaaaga aaaagtgttg agttggcttt tagggctaga gcaatgtatc ttaggctcac     240
ttaaggaagc tgtagagatg agcccaagga gggaaaccag aagagccccc caggctcacc     300
agttgtttgt tggctcccta caaacatgtc attcaagtgg ctaatcttac aacagcacaa     360
attcatctaa ccagaaagag aagaggaggc tccaaaggca cttgactact gagcatcacc     420
ctggacgtgt acaagtctgc gtccttattg ttttcttcat tgggccgaac tttctggtcc     480
tcatccaaca gctcttctat cacgtgttcg aaagtgtcag ccaatgatgt caagcctctt     540
gaacctgcct tgggcccatt cacgctctcc agagtcccat gggtccgcac acctggagat     600
actctattat agcaaagaag aaagataatt tcattgagcc atcctgtttt acaggaaatt     660
ctgcaagtgg caacgtgggt ccattccgtg tgtgtcacta gagctggcgc aagcccatgg     720
ccatggtgag gcagcgtttc cactggaact aatctgatac ctgcaccagc tcttgcaact     780
gtgcagtgtt cccactgcaa actacggatg gggtaaaaga ctgctcacct cctatttctc     840
atctaatctc acacactctg tttgatgagg ctatggagaa acaggtcttc tcatacacta     900
aaggtgggag tacaaacaat tcaagccctg tgcaggacaa ttaggcaata cctatcaaaa     960
ttatacatga ttttcctgc tgacccagca attccacttc tgggaataat tgacagatat    1020
aggtgcatat gtacaaaatg atggaaagct ctctggtata tattagtaag tgataaaaca    1080
aggtgtaaaa tagtgtatat atggctacta ccttttgttt taaaaatggg ggaaatggt     1140
ggagcttgcg gtgagccgag atcgtgccac tgcactccag cctgggcgac agagcgagac    1200
tccgtctcaa aaaaaaaaca gggtggggtg gggggaaat aatagtacat actcatattt    1260
acctgtatct atataaaaca cactatcaag gattcacaag aaactaatac aaatgatcac    1320
cttatagatg gtatgtattg ggggatactg aggtgagcag ggtataagtg gggcaagact    1380
tttcagtgta aacttctttt aaatttttatt ttgattttg aataatgtaa attaactgtc    1440
aaataattaa attaaaaata accaatttat taacaaaa                             1478
```

<210> SEQ ID NO 5
<211> LENGTH: 1437
<212> TYPE: DNA
<213> ORGANISM: Homo sapiens

<400> SEQUENCE: 5

```
atcgcgagat caggaaggtg gccgagtgtg tcgccgcggc catcaggcac ttctccttcc      60
tgcccttgta tgaagaagga tgtgtttgct tccccttgtg ccatgattgt aaatttcctg     120
aggcctcctc agccctgcag aactggctag agcaatgtat cttaggctca cttaaggaag     180
ctgtagagat gagcccaagg agggaaacca gaagagcccc caggctcac cagttgtttg     240
ttggctccct acaaacatgt cattcaagtg gctaatctta acagcacaca aattcatcta     300
accagaaaga gaagaggagg ctccaaaggc acttgactac tgagcatcac cctggacgtg     360
tacaagtctg cgtccttatt gttttcttca ttgggccgaa ctttctggtc ctcatccaac     420
```

```
agctcttcta tcacgtgttc gaaagtgtca gccaatgatg tcaagcctct tgaacctgcc      480
ttgggcccat tcacgctctc cagagtccca tgggtccgca cctggaga tactctatta        540 tagcaaagaa gaaagataat ttcattgagc catcctgttt tacaggaaat tctgcaagtg      600
gcaacgtggg tccattccgt gtgtgtcact agagctggcg caagcccatg gccatggtga      660
ggcagcgttt ccactggaac taatctgata cctgcaccag ctcttgcaac tgtgcagtgt      720
tcccactgca aactacggat ggggattttc cctcctggtg agtcaaaatg aacaagaaat      780
accccaggac ctcccttccc tccttggcca ttaatgagat gaaggcaatt aactcacata      840
gtataaatga atcatttgag gtgatgactg cattttaggc aaatgatgac tttcttggtt      900
ccattggttt gcaagtaaaa gttacacaca ttgaaaagac actgaaacag atttcctaaa      960
tgcttcattt tctggatgca ccaatgttga cctactatac atgttaaatg gttttaaaat     1020
atcaccttaa aataaaggaa acttccagct actaactcag ctctgaatgg gctatgaaag     1080
gctccaaagg tatgtgaaaa attactgtta ttttgcttta aaaaatgtga tgtctaagag     1140
tgtctgcaat gttctaatgc ttcaaaacat gtacgtaagc cttgtttatc tggaaatcat     1200
ttctttctgc ttatatcatt tataaataga aaatgttctg taataactta aaatagttcc     1260
acatacataa tgcttttagt gtcataatac ttactactgg tctatattta ccaacattta     1320
tcacatttta caaatgaag tagaagaaaa aaaagacaac gactttatgg ccctggaatt      1380
ccagtaatgg tgaccaacat gttttaaatt ccagtaaagg ttatggttac atttcaa        1437

<210> SEQ ID NO 6
<211> LENGTH: 2322
<212> TYPE: DNA
<213> ORGANISM: Homo sapiens

<400> SEQUENCE: 6
atcgcgagat caggaaggtg gccgagtgtg tcgccgcggc catcaggcac ttctccttcc       60
tgcccttgta tgaagaagga tgtgtttgct tcccccttgtg ccatgattgt aaatttcctg     120
aggcctcctc agccctgcag aactggggtt atagccatgt gactgatctt cgtccaagaa     180
tatgtaaaga aaaagtgttg agttggcttt tagggctaga gcaatgtatc ttaggctcac     240
ttaaggaagc tgtagagatg agcccaagga gggaaaccag aagagccccc caggctcacc     300
agttgtttgt tggctcccta caaacatgtc attcaagtgg ctaatcttac aacagcacaa     360
attcatctaa ccagaaagag aagaggaggc tccaaaggca cttgactact gagcatcacc     420
ctggacgtgt acaagtctgc gtccttattg ttttcttcat tgggccgaac tttctggtcc     480
tcatccaaca gctcttctat cacgtgttcg aaagtgtcag ccaatgatgt caagcctctt     540
gaacctgcct tgggcccatt cacgctctcc agagtcccat gggtccgcac acctggagat     600
actctattat agcaaagaag aaagataatt tcattgagcc atcctgtttt acagtattga     660
attattacca caaggtacca accatatatg catacttaat agggtatttt gtcaaaacta     720
tgcatgaagg tcatttgttt gagatgtcag aacattttcc cgtgagaaga tctcattggg     780
cattgaaaca gaaccacatg ctcttcagac cagcaaccgc gactaccaaa tactcctctg     840
tcaactctac ttgagtaaga acgctttcaa ttaaggccta agtgtcaaca tgcctttaaa     900
aaaaatcgtg gtgacacaaa atctttcttt ttagcaccca acagaatccc ttcaaagcct     960
cgtggtctga caccctatgc tacgtgactt gtgacccatc catttgtcat gttcttcggg    1020
aatgtggcta aggggctaag atgtgacttg aaaagaaagg tagaacaaga tcatctcaaa    1080
tttattatca aggaatagtt cagaaaacga cttcagacca cagagacagc agaacagatg    1140
```

-continued

| | |
|---|---|
| gtccggcatg gatagagcat cagacactca cagactgtgc caacaagagc catcgagtca | 1200 |
| aaacagccaa aggaaggagg gtcatggaat gggttctctc acaccaaact gatgcccaga | 1260 |
| ggccctcagc atgaataaca aaggcaacca gacccacaag ccatactgag tggatacaaa | 1320 |
| acctatacct aggctgacat cccaaatgtg tgtggcaagt tagatgatga tggcacaaaa | 1380 |
| gacagaacac cttgcttctg gccattgtca gctcttggaa gagagcacac ttttagagga | 1440 |
| gcagctgcaa ggagcctgag aacaaaactg gaaatgtctg ttatgaaagc cttcacagga | 1500 |
| aattctgcaa gtggcaacgt gggtccattc cgtgtgtgtc actagagctg gcgcaagccc | 1560 |
| atggccatgg tgaggcagcg tttccactgg aactaatctg atacctgcac cagctcttgc | 1620 |
| aactgtgcag tgttcccact gcaaactacg gatggggtaa aagactgctc acctcctatt | 1680 |
| tctcatctaa tctcacacac tctgtttgat gaggctatgg agaaacaggt cttctcatac | 1740 |
| actaaaggtg ggagtacaaa caattcaagc cctgtgcagg acaattaggc aatacctatc | 1800 |
| aaaattatac atgattttc ctgctgaccc agcaattcca cttctgggaa taattgacag | 1860 |
| atataggtgc atatgtacaa aatgatggaa agctctctgg tatatattag taagtgataa | 1920 |
| aacaaggtgt aaaatagtgt atatatggct actaccttt gttttaaaaa tgggggaaaa | 1980 |
| tggtggagct tgcggtgagc cgagatcgtg ccactgcact ccagcctggg cgacagagcg | 2040 |
| agactccgtc tcaaaaaaaa aacagggtgg ggtgggggg aataatagt acatactcat | 2100 |
| atttacctgt atctatataa aacacactat caaggattca caagaaacta atacaaatga | 2160 |
| tcaccttata gatggtatgt attggggat actgaggtga gcagggtata agtggggcaa | 2220 |
| gacttttcag tgtaaacttc ttttaaattt tatttgatt tttgaataat gtaaattaac | 2280 |
| tgtcaaataa ttaaattaaa ataaccaat ttattaacaa aa | 2322 |

```
<210> SEQ ID NO 7
<211> LENGTH: 2036
<212> TYPE: DNA
<213> ORGANISM: Homo sapiens

<400> SEQUENCE: 7
```

| | |
|---|---|
| atcgcgagat caggaaggtg gccgagtgtg tcgccgcggc catcaggcac ttctccttcc | 60 |
| tgcccttgta tgaagaagga tgtgtttgct tccccttgtg ccatgattgt aaatttcctg | 120 |
| aggcctcctc agccctgcag aactggctag agcaatgtat cttaggctca cttaaggaag | 180 |
| ctgtagagat gagcccaagg agggaaacca gaagagcccc ccaggctcac cagttgtttg | 240 |
| ttggctccct acaaacatgt cattcaagtg gctaatctta aacagcaca aattcatcta | 300 |
| accagaaaga gaagaggagg ctccaaaggc acttgactac tgagcatcac cctggacgtg | 360 |
| tacaagtctg cgtccttatt gttttcttca ttgggccgaa cttctggtc ctcatccaac | 420 |
| agctcttcta tcacgtgttc gaaagtgtca gccaatgatg tcaagcctct tgaacctgcc | 480 |
| ttgggcccat tcacgctctc cagagtccca tgggtccgca cacctggaga tactctatta | 540 |
| tagcaaagaa gaaagataat ttcattgagc catcctgttt tacagcaccc aacagaatcc | 600 |
| cttcaaagcc tcgtggtctg acaccctatg ctacgtgact tgtgacccat ccatttgtca | 660 |
| tgttcttcgg gaatgtggct aaggggctaa gatgtgactt gaaagaaag gtagaacaag | 720 |
| atcatctcaa atttattatc aaggaatagt tcagaaaacg acttcagacc acagagacag | 780 |
| cagaacagat ggtccggcat ggatagagca tcagacactc acagactgtg ccaacaagag | 840 |
| ccatcgagtc aaaacagcca aggaaggag ggtcatggaa tgggttctct cacaccaaac | 900 |
| tgatgcccag aggccctcag catgaataac aaaggcaacc agacccacaa gccatactga | 960 |

```
gtggatacaa aacctatacc taggctgaca tcccaaatgt gtgtggcaag ttagatgatg    1020
atggcacaaa agacagaaca ccttgcttct ggccattgtc agctcttgga agagagcaca    1080
cttttagagg agcagctgca aggagcctga gaacaaaact ggaaatgtct gttatgaaag    1140
ccttcacagg aaattctgca agtggcaacg tgggtccatt ccgtgtgtgt cactagagct    1200
ggcgcaagcc catggccatg gtgaggcagc gtttccactg gaactaatct gatacctgca    1260
ccagctcttg caactgtgca gtgttccac tgcaaactac ggatgggaga ggataaagaa    1320
cttcaatctt taaaaagag aggattttcc ctcctggtga gtcaaaatga acaagaaata    1380
ccccaggacc tcccttccct ccttggccat aatgagatg aaggcaatta actcacatag    1440
tataaatgaa tcatttgagg tgatgactgc attttaggca aatgatgact ttcttggttc    1500
cattggtttg caagtaaaag ttacacacat tgaaaagaca ctgaaacaga tttcctaaat    1560
gcttcatttt ctggatgcac caatgttgac ctactataca tgttaaatgg ttttaaaata    1620
tcaccttaaa ataaaggaaa cttccagcta ctaactcagc tctgaatggg ctatgaaagg    1680
ctccaaaggt atgtgaaaaa ttactgttat tttgctttaa aaaatgtgat gtctaagagt    1740
gtctgcaatg ttctaatgct tcaaaacatg tacgtaagcc ttgtttatct ggaaatcatt    1800
tctttctgct tatatcattt ataaatgaaa atgttctgt aataacttaa aatagttcca    1860
catacataat gcttttagtg tcataatact tactactggt ctatatttac caacatttat    1920 cacatttttac aaaatgaagt agaagaaaaa aagacaacg actttatggc cctggaattc    1980
cagtaatggt gaccaacatg ttttaaattc cagtaaaggt tatggttaca tttcaa        2036

<210> SEQ ID NO 8
<211> LENGTH: 2364
<212> TYPE: DNA
<213> ORGANISM: Homo sapiens

<400> SEQUENCE: 8
gtcatcgctg tctggaacag cgatgactcg atcgcgagat caggaaggtg gccgagtgtg      60
tcgccgcggc catcaggcac ttctccttcc tgcccttgta tgaagaagga tgtgtttgct     120
tccccttgtg ccatgattgt aaatttcctg aggcctcctc agccctgcag aactggggtt     180
atagccatgt gactgatctt cgtccaagaa tatgtaaaga aaaagtgttg agttggcttt     240
tagggctaga gcaatgtatc ttaggctcac ttaaggaagc tgtagagatg agcccaagga     300
gggaaaccag aagagccccc caggctcacc agttgtttgt tggctcccta caaacatgtc     360
attcaagtgg ctaatcttac aacagcacaa attcatctaa ccagaaagag aagaggaggc     420
tccaaaggca cttgactact gagcatcacc ctggacgtgt acaagtctgc gtccttattg     480 tttcttcat tgggccgaac tttctggtcc tcatccaaca gctcttctat cacgtgttcg     540
aaagtgtcag ccaatgatgt caagcctctt gaacctgcct tgggcccatt cacgctctcc     600
agagtcccat gggtccgcac acctggagat actctattat agcaaagaag aaagataatt     660
tcattgagcc atcctgtttt acagtattga attattacca caaggtacca accatatatg     720
catacttaat agggtatttt gtcaaaacta tgcatgaagg tcatttgttt gagatgtcag     780
aacattttcc cgtgagaaga tctcattggg cattgaaaca gaaccacatg ctcttcagac     840
cagcaaccgc gactaccaaa tactcctctg tcaactctac ttgagtaaga acgctttcaa     900
ttaaggccta agtgtcaaca tgccttaaaa aaaatcgtg gtgacacaaa atctttcttt     960
ttagcaccca acagaatccc ttcaaagcct cgtggtctga cacctatgc tacgtgactt    1020 gtgacccatc catttgtcat gttcttcggg aatgtggcta aggggctaag atgtgacttg    1080
```

| | |
|---|---|
| aaaagaaagg tagaacaaga tcatctcaaa tttattatca aggaatagtt cagaaaacga | 1140 |
| cttcagacca cagagacagc agaacagatg gtccggcatg gatagagcat cagacactca | 1200 |
| cagactgtgc caacaagagc catcgagtca aaacagccaa aggaaggagg gtcatggaat | 1260 |
| gggttctctc acaccaaact gatgcccaga ggccctcagc atgaataaca aaggcaacca | 1320 |
| gacccacaag ccatactgag tggatacaaa acctatacct aggctgacat cccaaatgtg | 1380 |
| tgtggcaagt tagatgatga tggcacaaaa gacagaacac cttgcttctg gccattgtca | 1440 |
| gctcttggaa gagagcacac ttttagagga gcagctgcaa ggagcctgag aacaaaactg | 1500 |
| gaaatgtctg ttatgaaagc cttcacagga aattctgcaa gtggcaacgt gggtccattc | 1560 |
| cgtgtgtgtc actagagctg gcgcaagccc atggccatgg tgaggcagcg tttccactgg | 1620 |
| aactaatctg atacctgcac cagctcttgc aactgtgcag tgttcccact gcaaactacg | 1680 |
| gatggggtaa aagactgctc acctcctatt tctcatctaa tctcacacac tctgtttgat | 1740 |
| gaggctatgg agaaacaggt cttctcatac actaaaggtg ggagtacaaa caattcaagc | 1800 |
| cctgtgcagg acaattaggc aatacctatc aaaattatac atgattttc ctgctgaccc | 1860 |
| agcaattcca cttctgggaa taattgacag atataggtgc atatgtacaa aatgatggaa | 1920 |
| agctctctgg tatatattag taagtgataa acaaggtgta aaaatagtgt atatatggct | 1980 |
| actacctttt gttttaaaaa tgggggaaaa tggtggagct tgcggtgagc cgagatcgtg | 2040 |
| ccactgcact ccagcctggg cgacagagcg agactccgtc tcaaaaaaaa aacagggtgg | 2100 |
| ggtgggggg aaataatagt acatactcat atttacctgt atctatataa aacacactat | 2160 |
| caaggattca caagaaacta atacaaatga tcaccttata gatggtatgt attgggggat | 2220 |
| actgaggtga gcagggtata agtggggcaa gacttttcag tgtaaacttc ttttaaattt | 2280 |
| tattttgatt tttgaataat gtaaattaac tgtcaaataa ttaaattaaa aataaccaat | 2340 |
| ttattaacaa aaaaaaaaaa aaaa | 2364 |

<210> SEQ ID NO 9
<211> LENGTH: 3136
<212> TYPE: DNA
<213> ORGANISM: Homo sapiens

<400> SEQUENCE: 9

| | |
|---|---|
| ctgcataaag atttcttcac agggtccttt aaaactgtct atttctaaga ggtcccttcc | 60 |
| actacaggta aaaggaaatt ccctctaccc tagggcccct caggatccct tcctctctca | 120 |
| cacgtttctt cgactgctcc tgatttaagc attcagctgg ccacgcaacg caagaagcaa | 180 |
| taagaacaca aaaaccctac cctgttcctc ctctatccgt ggcctttgcc accacctcca | 240 |
| caacctagtt cagattcctc ttcttttctc aagggaacgt ctaaagctct caagtccgtt | 300 |
| ttggcagggc gattttgtaa gtctgaaaca tttcagtgtg tctctcgatc tcaggcagct | 360 |
| caaaagaaaa gatctgctgg ctgcgtgaag gtgcattaga aacctgctgc taccttgcag | 420 |
| cctgggctga gcatatgctc cggaacttgc ttctcttcca acatcctgca cctcagggtt | 480 |
| gcacgctctg gttcccaaac ccccggccgc tggcttatgc aaatcactta ggtacatgca | 540 |
| aaagtatccc ttctcccgga gcgccattgg cccggggagg tctcgagctc attactatgc | 600 |
| agagaggaga gccgccattg ccaagagga ggaccagagg ggcgtgtttc tcgggcaaat | 660 |
| tggatctcct aaaattggatg acctgggctg aaagacaact taaagacccc cagaaaactc | 720 |
| tggttttata gataagaaat ctgaggctcg agagagagtg tgttctgccc aacatcatca | 780 |
| cggaacagct cctgggctcc tggctcctaa tctgatcgcg agatcaggaa ggtggccgag | 840 |

```
tgtgtcgccg cggccatcag gcacttctcc ttcctgccct gtatgaaga aggatgtgtt    900
tgcttcccct tgtgccatga ttgtaaattt cctgaggcct cctcagccct gcagaactgg    960
ggttatagcc atgtgactga tcttcgtcca agaatatgta agaaaaagt gttgagttgg    1020
cttttagggc tagagcaatg tatcttaggc tcacttaagg aagctgtaga gatgagccca    1080
aggagggaaa ccagaagagc cccccaggct caccagttgt tgttggctc cctacaaaca    1140
tgtcattcaa gtggctaatc ttacaacagc acaaattcat ctaaccagaa agagaagagg    1200
aggctccaaa ggcacttgac tactgagcat caccctggac gtgtacaagt ctgcgtcctt    1260
attgttttct tcattgggcc gaactttctg gtcctcatcc aacagctctt ctatcacgtg    1320
ttcgaaagtg tcagccaatg atgtcaagcc tcttgaacct gccttgggcc cattcacgct    1380
ctccagagtc ccatgggtcc gcacacctgg agatactcta ttatagcaaa gaagaaagat    1440
aatttcattg agccatcctg ttttacagta ttgaattatt accacaaggt accaaccata    1500
tatgcatact taatagggta ttttgtcaaa actatgcatg aaggtcattt gtttgagatg    1560
tcagaacatt ttcccgtgag aagatctcat tgggcattga acagaaacca catgctcttc    1620
agaccagcaa ccgcgactac caaatactcc tctgtcaact ctacttgagt aagaacgctt    1680
tcaattaagg cctaagtgtc aacatgcctt taaaaaaaat cgtggtgaca caaatctttt    1740
cttttagca cccaacagaa tcccttcaaa gcctcgtggt ctgacaccct atgctacgtg    1800
acttgtgacc catccatttg tcatgttctt cgggaatgtg gctaagggc taagatgtga    1860
cttgaaaaga aggtagaac aagatcatct caaatttatt atcaaggaat agttcagaaa    1920
acgacttcag accacagaga cagcagaaca gatggtccgg catggataga gcatcagaca    1980
ctcacagact gtgccaacaa gagccatcga gtcaaaacag ccaaaggaag gagggtcatg    2040
gaatgggttc tctcacacca aactgatgcc cagaggccct cagcatgaat aacaaaggca    2100
accagaccca caagccatac tgagtggata caaaacctat acctaggctg acatcccaaa    2160
tgtgtgtggc aagttagatg atgatggcac aaaagacaga acaccttgct tctggccatt    2220
gtcagctctt ggaagagagc acacttttag aggagcagct gcaaggagcc tgagaacaaa    2280
actggaaatg tctgttatga agccttcac aggaaattct gcaagtggca acgtgggtcc    2340
attccgtgtg tgtcactaga gctggcgcaa gcccatggcc atggtgaggc agcgtttcca    2400
ctggaactaa tctgataccct gcaccagctc ttgcaactgt gcagtgttcc cactgcaaac    2460
tacgatgggg gtaaaagact gctcacctcc tatttctcat ctaatctcac acactctgtt    2520
tgatgaggct atggagaaac aggtcttctc atacactaaa ggtgggagta caaacaattc    2580
aagccctgtg caggacaatt aggcaatacc tatcaaaatt atacatgatt tttcctgctg    2640
acccagcaat tccacttctg ggaataattg acagatatag gtgcatatgt acaaaatgat    2700
ggaaagctct ctggtatata ttagtaagtg ataaaacaag gtgtaaaata gtgtatatat    2760
ggctactacc ttttgtttta aaatgggggg aaaatggtgg agcttgcggt gagccgagat    2820
cgtgccactg cactccagcc tgggcgacag agcgagactc cgtctcaaaa aaaaaacagg    2880
gtggggtggg gggaaataa tagtacatac tcatatttac ctgtatctat ataaaacaca    2940
ctatcaagga ttcacaagaa actaatacaa atgatcacct tatagatggt atgtattggg    3000
ggatactgag gtgagcaggg tataagtggg gcaagacttt tcagtgtaaa cttcttttaa    3060
attttatttt gattttgtgaa taatgtaaat taactgtcaa ataattaaat taaaaataac    3120
caatttatta acaaaa                                                     3136
```

```
<210> SEQ ID NO 10
<211> LENGTH: 906
<212> TYPE: DNA
<213> ORGANISM: Mus musculus

<400> SEQUENCE: 10
cgctgtctca atataatcta tacaacataa atccactatc ttcccctttt aatggtcagt      60
gtacatacac aggaagtgtc tatccttatg aatcgccagc caattctctt tttgctatcc     120
atagtaaggg cccgaacata cgattgggta gttcggcatt gcgagttcca gtgccttttg     180
tctatgcccc tgcagccttc cttggtgtaa cccatgggat tacacttggt ctcgtagaaa     240
tactgcttca gttggccttt ggataccggg actttctcta ggactgtgac cgtcccgcca     300
gacatgtcca ctgcagtctt tttatctgcc gctgtgaccc actcgctaat actgtcacac     360
acgctcagct ccccacggcg ggcagggtcg gagtggcgcc gaaccctcat agacatgttt     420
gcggcatcca ggtaattttt gtattcctcc agcagaaaga gtagaggagg ctccaaaggc     480
acttgactgc tgagcatcac ccgggaagtg tacaagtccg cgtccttatg gttttcttcg     540
ttgggccgaa ccttctggtc ctcatccagc agctcttcga tgacgtgctc aaaagtgtca     600
gccagtgatg tcgtcgtcag acctctcgaa cctgccctgg gcccattcac gctctccaga     660
gtcccatggg tccgcacacc tgggtaggcc aagttgcctt gtccgtggac gtttacttct     720
ttcatgggcg ccgccttcat gcaaccgaag tatgaaataa ccatagtaag gaaaaggatg     780
gtcatcactc ttctcaccctg gtggaactgt gggaaggaag cagagacaga cacagaacag     840
gttagaactt ctttctcggg gacagcatgt ggcccatctg cttcaataat ttaatttaaa     900
aaaaaa                                                                906

<210> SEQ ID NO 11
<211> LENGTH: 992
<212> TYPE: DNA
<213> ORGANISM: Mus musculus

<400> SEQUENCE: 11
cgctgtctca atataatcta tacaacataa atccactatc ttcccctttt aatggtcagt      60
gtacatacac aggaagtgtc tatccttatg aatcgccagc caattctctt tttgctatcc     120
atagtaaggg cccgaacata cgattgggta gttcggcatt gcgagttcca gtgccttttg     180
tctatgcccc tgcagccttc cttggtgtaa cccatgggat tacacttggt ctcgtagaaa     240
tactgcttca gttggccttt ggataccggg actttctcta ggactgtgac cgtcccgcca     300
gacatgtcca ctgcagtctt tttatctgcc gctgtgaccc actcgctaat actgtcacac     360
acgctcagct ccccacggcg ggcagggtcg gagtggcgcc gaaccctcat agacatgttt     420
gcggcatcca ggtaattttt gtattcctcc agcagaaaga gtagaggagg ctccaaaggc     480
acttgactgc tgagcatcac ccgggaagtg tacaagtccg cgtccttatg gttttcttcg     540
ttgggccgaa ccttctggtc ctcatccagc agctcttcga tgacgtgctc aaaagtgtca     600
gccagtgatg tcgtcgtcag acctctcgaa cctgccctgg gcccattcac gctctccaga     660
gtcccatggg tccgcacacc tgggtaggcc aagttgcctt gtccgtggac gtttacttct     720
ttcatgggcg ccgccttcat gcaaccgaag tatgaaataa ccatagtaag gaaaaggatg     780
gtcatcactc ttctcaccctg gtggaactgt gggaaggaag cagagacaga cacagaacag     840
gatggttggc tccagcctca ttccttctgt cccagcttct gaagttctgg gaatacaaca     900
```

```
tgtaccatca tgccaagctc tacttttga aatcatggct cctgatatgt tgggcagccc        960
tgttgtgctt tgaagataaa atgctccaca aa                                     992
```

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

```
aacaaacaac uggugagccu gg                                                 22
```

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ugagccuaag auacauugcu cu                                                 22
```

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14

```
gugcuguugu aagauuagcc ac                                                 22
```

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

```
aaugacaugu uuguagggag cc                                                 22
```

<210> SEQ ID NO 16
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

```
ccaggugugc ggac                                                          14
```

<210> SEQ ID NO 17
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 17
ccaugggacu cugg                                                          14

<210> SEQ ID NO 18
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
agagcgugaa uggg                                                          14

<210> SEQ ID NO 19
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cccaaggcag guuc                                                          14

<210> SEQ ID NO 20
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aagaugcuug acau                                                          14

<210> SEQ ID NO 21
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cauuggcuga cacu                                                          14

<210> SEQ ID NO 22
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uucgaacacg ugau                                                          14

<210> SEQ ID NO 23
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 23
agaagagcug uugg                                                         14

<210> SEQ ID NO 24
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
augaggacca gaaa                                                         14

<210> SEQ ID NO 25
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
guucggccca auga                                                         14

<210> SEQ ID NO 26
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
agaaaacaau aagg                                                         14

<210> SEQ ID NO 27
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
acgcagacuu guac                                                         14

<210> SEQ ID NO 28
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
acguccaggg ugau                                                         14

<210> SEQ ID NO 29
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 29
gcucaguagu caag                                                        14

<210> SEQ ID NO 30
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugccuuugga gccu                                                        14

<210> SEQ ID NO 31
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ccucuucucu uucu                                                        14

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cccggtatcc aaaggc                                                      16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtattagcga gtgggt                                                      16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtctatgagg gttcgg                                                      16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 35
cctcctctac tctttc                                                        16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggcaggttcg agaggt                                                        16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttccttccca cagttc                                                        16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cggttgcatg aaggcg                                                        16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tggctggcga ttcata                                                        16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caacatatca ggagcc                                                        16

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 41
tgtattccca gaactt                                                   16

<210> SEQ ID NO 42
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uaugguuauu ucauacuucg guugcaug                                      28

<210> SEQ ID NO 43
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
agaaguaaac guccacggac aaggcaac                                      28

<210> SEQ ID NO 44
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
auuucuacga gaccaagugu aaucccau                                      28

<210> SEQ ID NO 45
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uaaggacgcg gacuuguaca cuuccggg                                      28

<210> SEQ ID NO 46
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
agaaagaaag uucuaaccug uucugugu                                      28

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 47
gatttcagag ccgcag                                                    16

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gacacatcca tcccag                                                    16

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctcgtcatg tctgtg                                                    16

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cttgaattgt ttgta                                                     15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agttgcaaga gttgg                                                     15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atctgttctg ctgtc                                                     15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 53
catattcttg gacga                                                    15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgtgctgttg taaga                                                    15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgacagagga gtatt                                                    15

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ggcucaccag uuguuuguu                                                19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gcaauguauc uuaggcuca                                                19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gcuaaucuua caacagcac                                                19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 59
ucccuacaaa caugucauu                                                19

<210> SEQ ID NO 60
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gcaaccgaag uaugaaauaa ccaua                                         25

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gccuuguccg uggacguuua cuucu                                         25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ggauuacacu uggucucgua gaaau                                         25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggaaguguac aaguccgcgu ccuua                                         25

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cagaacaggu uagaacuuuc uuucu                                         25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 65
gcacacctgg agatactcta ttata                                          25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctgcagaat ggcctggaat tacaa                                          25

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ccucuccacg cgcaguacat t                                              21

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccacgcgcag tacatg                                                    16
```

TREATMENT OF BRAIN DERIVED NEUROTROPHIC FACTOR (BDNF) RELATED DISEASES BY INHIBITION OF NATURAL ANTISENSE TRANSCRIPT TO BDNF

CROSS-REFERENCE TO RELATED APPLICATION

This application is a continuation of U.S. application Ser. No. 14/384,659, filed Sep. 11, 2014, which is a U.S. National Stage Entry of PCT/US2013/030589, filed Mar. 12, 2013, which claims the benefit of U.S. Prov. Pat. App. Ser. No. 61/611,225, filed on Mar. 15, 2012, and U.S. Prov. Pat. App. Ser. No. 61/614,664, filed on Mar. 23, 2012, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 30, 2018, is named "37092763301_SL.txt" and is 49,152 bytes in size.

FIELD OF THE INVENTION

Embodiments of the invention comprise oligonucleotides modulating expression and/or function of BDNF and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

WO 2010/093904 and its US counterpart US/2011/0319475 disclose BDNF as a target for modulation using oligonucleotides recited therein. There is a need for continued development with respect to natural antisense targets and newly developed oligonucleotides that complement such targets and modulate BDNF protein expression to potentially treat or be used in research associated with treating BDNF related diseases and conditions.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding BDNF sense gene in mammalian organisms. It is also contemplated herein that inhibition of the natural antisense transcripts recited herein can be achieved by siRNA, ribozymes and small molecules, which are considered to be within the scope of the present invention.

One embodiment provides a method of modulating function and/or expression of a BDNF polynucleotide in biological systems, including, but not limited to, patient cells or tissues in vivo or in vitro comprising contacting said biological system or said cells or tissues with an antisense oligonucleotide of about 5 to about 30 nucleotides in length wherein said oligonucleotide has at least 50% sequence identity to a reverse complement of a polynucleotide comprising 5 to 30 consecutive nucleotides within nucleotides 1 to 1279 of SEQ ID NO: 3 or 1 to 1478 of SEQ ID NO: 4 or 1 to 1437 of SEQ ID NO: 5 or 1 to 2322 of SEQ ID NO: 6 or 1 to 2036 of SEQ ID NO: 7 or 1 to 2364 of SEQ ID NO: 8 or 1 to 3136 of SEQ ID NO: 9 or 1 to 906 of SEQ ID NO: 10 or 1 to 992 of SEQ ID NO: 11 thereby modulating function and/or expression of the BDNF polynucleotide in said biological system including said patient cells or tissues in vivo or in vitro, with the proviso that the oligonucleotides having SEQ ID NOS 50-55 are excluded.

In an embodiment, an oligonucleotide recited above targets a natural antisense sequence of BDNF polynucleotides present in a biological system, for example, nucleotides set forth in SEQ ID NOS: 3 to 11, and any variants, alleles, homologs, mutants, derivatives, fragments and complementary sequences thereto. Examples of such antisense oligonucleotides are set forth as SEQ ID NOS: 12 to 49.

In another embodiment, the invention comprises a method of modulating the function or expression of a BDNF polynucleotide in a biological system comprising contacting said biological system with at least one antisense oligonucleotide that targets a natural antisense transcript of the BDNF polynucleotide comprising 5 to 30 consecutive nucleotides within nucleotides 1 to 1279 of SEQ ID NO: 3 or 1 to 1478 of SEQ ID NO: 4 or 1 to 1437 of SEQ ID NO: 5 or 1 to 2322 of SEQ ID NO: 6 or 1 to 2036 of SEQ ID NO: 7 or 1 to 2364 of SEQ ID NO: 8 or 1 to 3136 of SEQ ID NO: 9 or 1 to 906 of SEQ ID NO: 10 or 1 to 992 of SEQ ID NO: 11 thereby modulating the function and/or expression of the BDNF polynucleotide in said biological system.

In another embodiment, the invention comprises a method of modulating the function or expression of a BDNF polynucleotide in a biological system comprising contacting said biological system with at least one antisense oligonucleotide that targets a region of a natural antisense transcript of the BDNF polynucleotide comprising 5 to 30 consecutive nucleotides within nucleotides 1 to 1279 of SEQ ID NO: 3 or 1 to 1478 of SEQ ID NO: 4 or 1 to 1437 of SEQ ID NO: 5 or 1 to 2322 of SEQ ID NO: 6 or 1 to 2036 of SEQ ID NO: 7 or 1 to 2364 of SEQ ID NO: 8 or 1 to 3136 of SEQ ID NO: 9 or 1 to 906 of SEQ ID NO: 10 or 1 to 992 of SEQ ID NO: 11 thereby modulating the function and/or expression of the BDNF polynucleotide in said biological system.

In an embodiment, the invention comprises a method of increasing the function and/or expression of a BDNF polynucleotide having SEQ ID NO. 1 and 2 in a biological system comprising contacting said biological system with at least one antisense oligonucleotide that targets a natural antisense transcript of said BDNF polynucleotide comprising 5 to 30 consecutive nucleotides within nucleotides 1 to 1279 of SEQ ID NO: 3 or 1 to 1478 of SEQ ID NO: 4 or 1 to 1437 of SEQ ID NO: 5 or 1 to 2322 of SEQ ID NO: 6 or 1 to 2036 of SEQ ID NO: 7 or 1 to 2364 of SEQ ID NO: 8 or 1 to 3136 of SEQ ID NO: 9 or 1 to 906 of SEQ ID NO: 10 or 1 to 992 of SEQ ID NO: 11 thereby increasing the function and/or expression of said BDNF polynucleotide or expression product thereof.

In another embodiment, the invention comprises a method of method of increasing the function and/or expression of a BDNF polynucleotide having SEQ ID NO. 1 and 2 in a biological system comprising contacting said biological system with at least one antisense oligonucleotide that targets a natural antisense transcript of said BDNF polynucleotide thereby increasing the function and/or expression of said BDNF polynucleotide or expression product thereof wherein the natural antisense transcripts are selected from SEQ ID NOS. 3 to 11.

In another embodiment, the invention comprises a method of method of increasing the function and/or expression of a BDNF polynucleotide having SEQ ID NO. 1 and 2 in a biological system comprising contacting said biological system with at least one antisense oligonucleotide that targets a natural antisense transcript of said BDNF polynucleotide thereby increasing the function and/or expression of said BDNF polynucleotide or expression product thereof wherein the natural antisense transcripts are selected from SEQ ID NOS. 3 to 11 and wherein the antisense oligonucleotides are selected from at least one of SEQ ID NOS. 12 to 49.

In an embodiment, a composition comprises one or more antisense oligonucleotides which bind to sense and/or antisense BDNF polynucleotides.

In an embodiment, the oligonucleotides comprise one or more modified or substituted nucleotides.

In an embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In an embodiment, the oligonucleotides are administered to a patient subcutaneously, intramuscularly, intravenously or intraperitoneally.

In an embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In an embodiment, the oligonucleotides are encapsulated in a liposome or attached to a carrier molecule (e.g. cholesterol, TAT peptide).

In an embodiment, the present invention comprises the use of SEQ ID NOS 50-55 as oligonucleotides targeting the natural antisense transcripts (NATs) to modulate the expression of a BDNF polynucleotide wherein said NATs are selected from the group consisting of SEQ ID NOS. 3 to 11. In another embodiment, the present invention comprises the use of SEQ ID NOS 50-55 as oligonucleotides targeting the natural antisense transcripts (NATs) to modulate the expression of a BDNF polynucleotide wherein said NATs are selected from the group consisting of SEQ ID NOS. 3, 4, 5, 7, 8, 9, 10 and 11.

Other aspects are described infra.

BRIEF DESCRIPTION OF THE DRAWINGS

FIG. 1A shows that after transfection of several human and mouse cell lines with three siRNA oligonucleotides, targeted to non-overlapping regions of the BDNF-AS transcript, knockdown and upregulation of BDNF transcript occurred. FIG. 1B shows time course study data after administration of BDNF-AS-targeted siRNA in the endogenous expression of both BDNF and BDNF-AS transcripts. The data shows that over the course of time BDNF-AS is downregulated and then BDNF expression is upregulated and is reversible. FIG. 1C shows that BDNF protein, measured by ELISA, was significantly increased with two siRNAs targeting BDNF-AS transcript, but not with scrambled siRNAs or a control nontargeting siRNA. FIG. 1D shows protein levels of BDNF following administration of various siRNAs using ELISA and/or western blotting. FIG. 1E shows the fold change percentage of BDNF compared to mock control versus increasing concentrations of oligonucleotide ($10^{-12}$ to $10^{-6}$ M).

FIG. 3A-3E shows BDNF-AS regulates Bdnf mRNA and protein in vivo.

FIG. 4A-4E shows Blocking of BDNF-AS, in vivo, causes an increase in neuronal survival and proliferation.

FIG. 5A-5B shows BDNF-AS knockdown leads to BDNF mRNA upregulation.

FIG. 6 shows Posttranscriptional regulation of Bdnf expression.

Figure 1A:
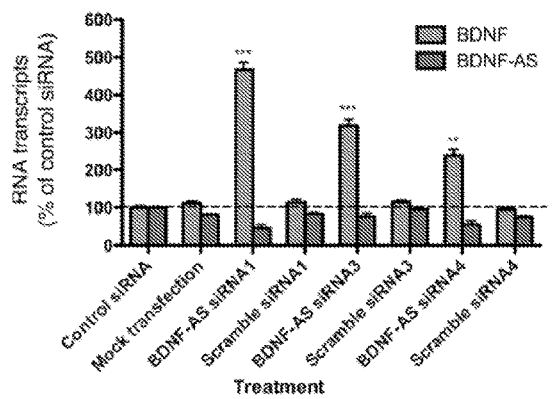
FIGS. 1A-1E show antisense-mediated regulation of sense mRNA and protein.

Sequence Listing Description: SEQ ID NO: 1: *Homo sapiens* Brain derived neurotrophic factor (BDNF), transcript variant 3, mRNA. (NCBI Accession No.: NM_170735); SEQ ID NO: 2: *Mus musculus* brain derived neurotrophic factor (Bdnf), transcript variant 1, mRNA (NCBI Accession No.: NM_007540); SEQ ID NO: 3: Natural BDNF antisense sequence (transcript variant BT1A; NR_033313.1); SEQ ID NO: 4: Natural BDNF antisense sequence (transcript variant BT2A; NR_033314.1); SEQ ID NO: 5: Natural BDNF antisense sequence (transcript variant BT1B; NR_033315.1); SEQ ID NO: 6: Natural BDNF antisense sequence (transcript variant BT2B; NR_002832.2); SEQ ID NO: 7: Natural BDNF antisense sequence (transcript variant BT1C; NR_033312.1); SEQ ID NO: 8: Natural BDNF antisense sequence (BDNF-AS variant); SEQ ID NO: 9: Natural BDNF antisense sequence; SEQ ID NO: 10: Mouse natural BDNF antisense sequence (Mouse BDNF-AS variant 1); SEQ ID NO: 11: Mouse natural BDNF antisense sequence (Mouse BDNF-AS variant 2); SEQ ID NOS: 12 to 55: Antisense oligonucleotides; SEQ ID NOS: 56 to 59: Reverse complement of the antisense oligonucleotides SEQ ID NOS: 12 to 15 respectively; SEQ ID NOS: 60 to 64: Reverse complement of the antisense oligonucleotides of SEQ ID NOS: 42 to 46 respectively; SEQ ID NOS: 65 and 66: Assay sequences. LNA (2'-0,4'-C methylene locked nucleic acid): indicated by "+," e.g., +A or +T or +C or +G; 2'OM (2'-O-methyl): indicated by "m," e.g., mU or mA or mC or mG; PS (phosphothioate bond): indicated by "*," e.g., T* or A* or G* or C*; RNA: indicated by "r," e.g., rU or rA or rG or rC.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In an embodiment, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "BDNF" and "Brain derived neurotrophic factor" are inclusive of all family members, mutants, alleles, fragments, species, coding and noncoding sequences, sense and antisense polynucleotide strands, etc.

As used herein, the words 'Brain derived neurotrophic factor', 'Brain-derived neurotrophic factor' and BDNF, are considered the same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) 1 *American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.*, 25(22), 4429-4443, Toulmé, J. J., (2001) *Nature* Biotechnology 19:17-18; Manoharan M., (1999) *Biochemica et Biophysica Acta* 1489: 117-139; Freier S. M., (1997) *Nucleic Acid Research*, 25:4429-4443, Uhlman, E., (2000) *Drug Discovery & Development*, 3: 203-213, Herdewin P., (2000) *Antisense & Nucleic Acid Drug Dev.*, 10:297-310); 2'-O, 3'-C-linked [3.2.0] bicycloarabinonucleosides. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na+ or K+ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense compound which is 18 nucleotides in length having 4 (four) non-complementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant", when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radio-isotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, gastric cancer, pre-malignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

As used herein a "Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). A Neurological disease or disorder includes but is not limited to acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anrol-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy;

Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HlVassociated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; a neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

A "proliferative disease or disorder" includes, but is not limited to, hematopoietic neoplastic disorders involving hyperplastic/neoplastic cells of hematopoietic origin arising from myeloid, lymphoid or erythroid lineages, or precursor cells thereof. These include, but are not limited to erythroblastic leukemia, acute promyeloid leukemia (APML), chronic myelogenous leukemia (CML), lymphoid malignancies, including, but not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; hepatitis; sepsis; alcoholic liver disease; non-alcoholic steatosis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

Polynucleotide and Oligonucleotide Compositions and Molecules

Targets:

In one embodiment, the targets comprise nucleic acid sequences of Brain derived neurotrophic factor (BDNF), including without limitation sense and/or antisense noncoding and/or coding sequences associated with BDNF. PCT Pub. No. WO 2010/093904 and U.S. Pat. App. Pub. No. 2011/0319475, both titled "Treatment of Brain Derived Neurotrophic Factor (BDNF) Related Diseases by Inhibition of Natural Antisense Transcript to BDNF" and incorporated by reference herein in their entirety, disclose BDNF as a target for modulation using oligonucleotides as recited therein.

Neurotrophins are a class of structurally related growth factors that promote neural survival and differentiation. They stimulate neurite outgrowth, suggesting that they can promote regeneration of injured neurons, and act as target-derived neurotrophic factors to stimulate collateral sprouting in target tissues that produce the neurotrophi. Brain-derived neurotrophic factor (BDNF) was initially characterized as a basic protein present in brain extracts and capable of increasing the survival of dorsal root ganglia. When axonal communication with the cell body is interrupted by injury, Schwann cells produce neurotrophic factors such as nerve growth factor (NGF) and BDNF. Neurotrophins are released from the Schwann cells and dispersed diffusely in gradient fashion around regenerating axons, which then extend distally along the neurotrophins' density gradient. Local application of BDNF to transected nerves in neonatal rats has been shown to prevent massive death of motor neurons that follows axotomy. The mRNA titer of BDNF increases to several times the normal level four days after auxotomy and reaches its maximum at 4 weeks. Moreover, BDNF has been reported to enhance the survival of cholinergic neurons in culture.

In an embodiment, antisense oligonucleotides are used to prevent or treat diseases or disorders associated with BDNF family members. Exemplary Brain derived neurotrophic factor (BDNF) mediated diseases and disorders which can be treated with the antisense oligonucleotides of the invention and/or with cell/tissues regenerated from stem cells obtained using and/or having the antisense compounds comprise: a disease or disorder associated with abnormal function and/or expression of BDNF, a neurological disease or disorder, a disease or a disorder associated with defective neurogenesis; a neurodegenerative disease or disorder (e.g., Alzheimer's disease, Parkinson's disease, Huntington's disease, amyotrophic lateral sclerosis etc.); a neuropsychiatric disorder (depression, schizophrenia, schizofreniform disorder, schizoaffective disorder, and delusional disorder; anxiety disorders such as panic disorder, phobias (including agoraphobia), an obsessive-compulsive disorder, a posttraumatic stress disorder, a bipolar disorder, anorexia nervosa, bulimia nervosa), an autoimmune disorder (e.g., multiple sclerosis) of the central nervous system, memory loss, a long term or a short term memory disorder, benign forgetfulness, a childhood learning disorder, close head injury, an attention deficit disorder, neuronal reaction to viral infection, brain damage, narcolepsy, a sleep disorder (e.g., circadian rhythm disorders, insomnia and narcolepsy); severance of nerves or nerve damage, severance of cerebrospinal nerve cord (CNS) and a damage to brain or nerve cells, a neurological deficit associated with AIDS, a motor and tic disorder characterized by motor and/or vocal tics (e.g., Tourette's disorder, chronic motor or vocal tic disorder, transient tic disorder, and stereotypic movement disorder), a substance abuse disorder (e.g., substance dependence, substance abuse and the sequalae of substance abuse/dependence, such as substance-induced psychological disorder, substance withdrawal and substance-induced dementia or amnestic disorder), traumatic brain injury, tinnitus, neuralgia (e.g., trigeminal neuralgia) pain (e.g chronic pain, chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, pain associated with drug intake and recurrent acute pain, neuropathic pain), inappropriate neuronal activity resulting in neurodysthesias in a disease such as diabetes, an MS and a motor neuron disease, ataxias, muscular rigidity (spasticity), temporomandibular joint dysfunction, Reward deficiency syndrome (RDS), neurotoxicity caused by alcohol or substance abuse (e.g., ecstacy, methamphetamine etc.), mental retardation or cognitive impairment (e.g., nonsyndromic X-linked mental retardation, fragile X syndrome, Down's syndrome, autism), aphasia, Bell's palsy, Creutzfeldt-jacob disease, encephalitis, age related macular degeneration, ondine syndrome, WAGR syndrome, hearing loss, Rett syndrome, epilepsy, spinal cord injury, stroke, hypoxia, ischemia, brain injury, diabetic neuropathy, peripheral neuropathy, nerve transplantation complications, motor neuron disease, peripheral nerve injury, obesity, a metabolic syndrome, cancer, asthma, an atopic disease, inflammation, allergy, eczema, a neuro-oncological disease or disorder, neuro-immunological disease or disorder and neuro-otological disease or disorder; and a disease or disorder associated with aging and senescence.

The present invention provides a mechanism by which endogenous NATs suppress transcription of their sense gene counterparts. The invention provides that endogenous gene expression can be upregulated, in a locus specific manner by the removal or inhibition of the NATs, which are transcribed from most transcriptional units.

One embodiment of the present invention provides examples of functional ncRNAs that regulate protein output, the phenomenon applicable to many other genomic loci.

The Brain-derived Neurotrophic Factor (BDNF) is a member of the "neurotrophin" family of growth factors, essential for neuronal growth, maturation differentiation and maintenance. BDNF is also essential for neuronal plasticity and shown to be involved in learning, and memory processes. The BDNF locus is on chromosome 11 and shows active transcription from both strands, which leads to transcription of a noncoding NATs.

The present invention characterizes the regulatory role of this antisense RNA molecule, BDNF-AS that exerts a potent reciprocal and dynamic regulation over the expression of sense BDNF mRNA and protein, both in vitro and in vivo.

One embodiment of the present invention provides a strategy for upregulation of mRNA expression, using antisense RNA transcript inhibitory molecules, which are termed as AntagoNATs. AntagoNATs are described, e.g., in PCT Pub. No. WO 2012/068340, incorporated herein by reference in its entirety.

The number of ncRNAs in eukaryotic genomes have been shown to increase as a function of developmental complexity and there is, for example, a great deal of diversity in ncRNAs expressed in the nervous system. Over the past few years, there have been reports on functional NATs and showed their potential involvement in human disorders, including Alzheimer's disease, Parkinson's disease and Fragile X syndrome. Moreover, it has been reported that upregulation of CD97 sense gene can be attained by knockdown of its antisense RNA transcript. Upregulation of progesterone receptor (PR), and other endogenous transcripts was reported following targeting of promoter-derived noncoding RNAs. Transcriptional activation of p21 gene and Oct4 promoter were reported following NATs depletion. Antisense RNA-induced chromatin remodeling seems to be a feasible and dynamic mode of action for many low copy number NATs. If so, antisense RNA might predominantly exert local effects to maintain or modify chromatin structure, ultimately activating or suppressing sense gene expression.

PCR2 is a protein complex that consists of four core subunits: Eed, Suz12, RbAp48 and the catalytic Ezh2, that catalyzes the trimethylation of histone H3-lysine. (H3K27met3). Recent studies provide evidence for direct RNA-protein interaction between Ezh2 and many ncRNA transcripts. Other studies of X inactivation and HOX gene cluster show RNA transcripts to be involved in the PRC2-mediated induction of H3K27met3, repressive chromatin marks. PRC2 transcriptome profiling has identified over 9,000 PRC2-interacting RNAs in embryonic stem cells, many of them categorized as antisense RNA transcripts. Epigenetic silencing of p15 and DM1 genes were reported to involve heterochromatin formation by its antisense RNA. The traditional binary division of chromatin into hetero- or eu-chromatin categories might not be complete as recent work has shown that there are five principal chromatin types that are more dynamic and flexible than originally believed. Likely applicable to a large number of gene loci, NATs can be manipulated in order to obtain a locus-specific alteration in chromatin modification. As examples, it is shown that cleavage (by siRNA) or inhibition (by AntagoNATs) of the antisense transcripts of BDNF genes leads to the upregulation of corresponding mRNAs.

Neurotrophins belong to a class of secreted growth factors that enhance the survival, development, differentiation and function of neurons and BDNF is an important molecular mediator of synaptic plasticity. BDNF is suggested to synchronize neuronal and glial maturation, participate in axonal and dendritic differentiation and protect and enhance neuronal cell survival. Neurotrophin expression levels are impaired in neurodegenerative and in psychiatric and neurodevelopmental disorders. The upregulation of neurotrophins is believed to have beneficial effects on several neurological disorders. AntagoNATs can be used as a therapeutic strategy to inhibit BDNF-AS and consequently enhance neuronal proliferation and survival in a variety of disease states. It cannot be excluded that the herein described approach to upregulate the synthesis of endogenous BDNF molecules, presumed to contain natural modifications and to represent all known splice forms, will prove to be distinct, and perhaps superior, to administrating synthetic BDNF molecules.

In an embodiment, modulation of BDNF by one or more antisense oligonucleotides is administered to a patient in need thereof, to prevent or treat any disease or disorder related to BDNF abnormal expression, function, activity as compared to a normal control.

In an embodiment, the oligonucleotides are specific for natural antisense transcripts of BDNF recited herein, which includes, without limitation noncoding regions. The BDNF targets comprise variants of BDNF; mutants of BDNF, including SNPs; noncoding sequences of BDNF; alleles, fragments and the like. Preferably the oligonucleotide is an antisense RNA molecule.

In accordance with embodiments of the invention, the target nucleic acid molecule is not limited to BDNF polynucleotides alone but extends to any of the isoforms, receptors, homologs, non-coding regions and the like of BDNF.

In an embodiment, an oligonucleotide targets a natural antisense sequence (natural antisense to the coding and non-coding regions) of BDNF targets, including, without limitation, variants, alleles, homologs, mutants, derivatives, fragments and complementary sequences thereto. Preferably the oligonucleotide is an antisense RNA or DNA molecule.

In an embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In an embodiment, targeting of BDNF including without limitation, antisense sequences which are identified and expanded, using for example, PCR, hybridization etc., one or more of the sequences set forth as SEQ ID NOS: 3 to 11, and the like, modulate the expression or function of BDNF. In one embodiment, expression or function is up-regulated as compared to a control. In an embodiment, expression or function is down-regulated as compared to a control.

In an embodiment, oligonucleotides comprise nucleic acid sequences set forth as SEQ ID NOS: 12 to 49 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Brain derived neurotrophic factor (BDNF).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In an embodiment, the antisense oligonucleotides bind to the natural antisense sequences of Brain derived neurotrophic factor (BDNF) and modulate the expression and/or function of BDNF (SEQ ID NO: 1 and 2). Examples of antisense sequences include SEQ ID NOS: 3 to 55.

In an embodiment, the antisense oligonucleotides bind to one or more segments of Brain derived neurotrophic factor (BDNF) polynucleotides and modulate the expression and/ or function of BDNF. The segments comprise at least five consecutive nucleotides of the BDNF sense or antisense polynucleotides.

In an embodiment, the antisense oligonucleotides are specific for natural antisense sequences of BDNF wherein binding of the oligonucleotides to the natural antisense sequences of BDNF modulate expression and/or function of BDNF.

In an embodiment, oligonucleotide compounds comprise sequences set forth as SEQ ID NOS: 12 to 49, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formyl methionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Brain derived neurotrophic factor (BDNF), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In an embodiment, the antisense oligonucleotides bind to coding and/or non-coding regions of a target polynucleotide and modulate the expression and/or function of the target molecule.

In an embodiment, the antisense oligonucleotides bind to natural antisense polynucleotides and modulate the expression and/or function of the target molecule.

In an embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention.

Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid is a multi-step process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise micro-RNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1:

In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2:

In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In an embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Brain derived neurotrophic factor (BDNF) polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Brain derived neurotrophic factor (BDNF) polynucleotides. "Modulators" are those compounds that decrease or increase the expression of a nucleic acid molecule encoding BDNF and which comprise at least a 5-nucleotide portion that is complementary to a preferred target segment. The screening method comprises the steps of contacting a preferred target segment of a nucleic acid molecule encoding sense or natural antisense polynucleotides of BDNF with one or more candidate modulators, and selecting for one or more candidate modulators which decrease or increase the expression of a nucleic acid molecule encoding BDNF polynucleotides, e.g. SEQ ID NOS: 12 to 49. Once it is shown that the candidate modulator or modulators are capable of modulating (e.g. either decreasing or increasing) the expression of a nucleic acid molecule encoding BDNF polynucleotides, the modulator may then be employed in further investigative studies of the function of BDNF polynucleotides, or for use as a research, diagnostic, or therapeutic agent in accordance with the present invention.

Targeting the natural antisense sequence preferably modulates the function of the target gene. For example, the BDNF gene (e.g. accession number NM_170735 and NM_007540). In an embodiment, the target is an antisense polynucleotide of the BDNF gene. In an embodiment, an antisense oligonucleotide targets sense and/or natural antisense sequences of BDNF polynucleotides (e.g. accession number NM_170735 and NM_007540), variants, alleles, isoforms, homologs, mutants, derivatives, fragments and complementary sequences thereto. Preferably the oligonucleotide is an antisense molecule and the targets include coding and noncoding regions of antisense and/or sense BDNF polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In an embodiment, an antisense oligonucleotide targets Brain derived neurotrophic factor (BDNF) polynucleotides (e.g. accession number NM_170735 and NM_007540), variants, alleles, homologs, mutants, derivatives, fragments and complementary sequences thereto. Preferably the oligonucleotide is an antisense molecule.

In accordance with embodiments of the invention, the target nucleic acid molecule is not limited to BDNF alone but extends to any polynucleotide variant thereof and any polynucleotide that produces, affects, impacts or results in or relates to a BDNF expression product and/or any isoforms thereof.

In an embodiment, an oligonucleotide targets a natural antisense sequence of BDNF polynucleotides, for example, polynucleotides set forth as SEQ ID NOS: 3 to 11, and any variants, alleles, homologs, mutants, derivatives, fragments and complementary sequences thereto. Examples of antisense oligonucleotides are set forth as SEQ ID NOS: 12 to 49.

In one embodiment, the oligonucleotides are complementary to or bind to nucleic acid sequences of BDNF antisense, including without limitation noncoding sense and/or antisense sequences associated with BDNF polynucleotides and modulate expression and/or function of BDNF molecules.

In an embodiment, the oligonucleotides are complementary to or bind to nucleic acid sequences of BDNF natural antisense, set forth as SEQ ID NOS: 3 to 11, and modulate expression and/or function of BDNF molecules.

In an embodiment, oligonucleotides comprise sequences of at least 5 consecutive nucleotides of SEQ ID NOS: 12 to 49 and modulate expression and/or function of BDNF molecules.

The polynucleotide targets comprise BDNF, including family members thereof, variants of BDNF; mutants of BDNF, including SNPs; noncoding sequences of BDNF; alleles of BDNF; species variants, fragments and the like. Preferably the oligonucleotide is an antisense molecule.

In an embodiment, the oligonucleotide targeting BDNF polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In an embodiment, targeting of Brain derived neurotrophic factor (BDNF) polynucleotides, e.g. SEQ ID NOS: 3 to 55 modulate the expression or function of these targets. In one embodiment, expression or function is up-regulated as compared to a control. In an embodiment, expression or function is down-regulated as compared to a control.

In an embodiment, antisense compounds comprise sequences set forth as SEQ ID NOS: 12 to 49. These oligonucleotides can comprise one or more modified nucleotides, shorter or longer fragments, modified bonds and the like.

In an embodiment, SEQ ID NOS: 12 to 49 comprise one or more LNA nucleotides. Table 1 shows exemplary antisense oligonucleotides useful in the methods of the invention.

TABLE 1

| Sequence ID | Antisense Sequence Name | Sequence |
|---|---|---|
| SEQ ID NO: 12 | CUR-2046 (Antisense) | ArArCrArArArCrArArCrUrGrGrUrGrArGrCrCrUrGrG |
| SEQ ID NO: 13 | CUR-2047 Antisense) | rUrGrArGrCrCrUrArArGrArUrArCrArUrUrGrCrUrCrU |
| SEQ ID NO: 14 | CUR-2048 (Antisense) | rGrUrGrCrUrGrUrUrGrUrArArGrArUrUrArGrCrCrArC |
| SEQ ID NO: 15 | CUR-2049 (Antisense) | rArArUrGrArCrArUrGrUrUrGrUrArGrGrGrArGrCrC |
| SEQ ID NO: 16 | CUR-2050 | +C*mC*mA*+G*mG*mU*+G*mU*mG*mC*+G*mG*mA*+C |
| SEQ ID NO: 17 | CUR-2051 | +C*mC*mA*+U*mG*mG*+G*mA*mC*mU*+C*mU*mG*+G |
| SEQ ID NO: 18 | CUR-2052 | +A*mG*mA*+G*mC*mG*+U*mG*mA*mA*+U*mG*mG*+G |
| SEQ ID NO: 19 | CUR-2053 | +C*mC*mC*+A*mA*mG*+G*mC*mA*mG*+G*mU*mU*+C |
| SEQ ID NO: 20 | CUR-2054 | +A*mA*mG*+A*mU*mG*+C*mU*mU*mG*+A*mC*mA*+U |
| SEQ ID NO: 21 | CUR-2055 | +C*mA*mU*+U*mG*mG*+C*mU*mG*mA*+C*mA*mC*+U |
| SEQ ID NO: 22 | CUR-2056 | +U*mU*mC*+G*mA*mA*+C*mA*mC*mG*+U*mG*mA*+U |
| SEQ ID NO: 23 | CUR-2057 | +A*mG*mA*+A*mG*mA*+G*mC*mU*mG*+U*mU*mG*+G |
| SEQ ID NO: 24 | CUR-2058 | +A*mU*mG*+A*mG*mG*+A*mC*mC*mA*+G*mA*mA*+A |
| SEQ ID NO: 25 | CUR-2059 | +G*mU*mU*+C*mG*mG*+C*mC*mC*mA*+A*mU*mG*+A |
| SEQ ID NO: 26 | CUR-2060 | +A*mG*mA*+A*mA*mA*+C*mA*mA*mU*+A*mA*mG*+G |
| SEQ ID NO: 27 | CUR-2061 | +A*mC*mG*+C*mA*mG*+A*mC*mU*mU*+G*mU*mA*+C |
| SEQ ID NO: 28 | CUR-2062 | +A*mC*mG*+U*mC*mC*+A*mG*mG*mG*+U*mG*mA*+U |
| SEQ ID NO: 29 | CUR-2063 | +G*mC*mU*+C*mA*mG*+U*mA*mG*mU*+C*mA*mA*+G |

TABLE 1-continued

| Sequence ID | Antisense Sequence Name | Sequence |
|---|---|---|
| SEQ ID NO: 30 | CUR-2064 | +U*mG*mC*+C*mU*mU*+U*mG*mG*mA*+G*mC*mC*+U |
| SEQ ID NO: 31 | CUR-2065 | +C*mC*mU*+C*mU*mU*+C*mU*mC*mU*+U*mU*mC*+U |
| SEQ ID NO: 32 | CUR-2066 | +C*+C*+C*G*G*T*A*T*C*C*A*A*A*+G*+G*+C |
| SEQ ID NO: 33 | CUR-2067 | +G*+T*+A*T*T*A*G*C*G*A*G*T*G*+G*+G*+T |
| SEQ ID NO: 34 | CUR-2068 | +G*+T*+C*T*A*T*G*A*G*G*T*T*+C*+G*+G |
| SEQ ID NO: 35 | CUR-2069 | +C*+C*+T*C*C*T*C*T*A*C*T*C*T*+T*+T*+C |
| SEQ ID NO: 36 | CUR-2070 | +G*+G*+C*A*G*T*T*C*G*A*G*A*+G*+G*+T |
| SEQ ID NO: 37 | CUR-2071 | +T*+T*+C*C*T*T*C*C*C*A*C*A*+G*+T*+T*+C |
| SEQ ID NO: 38 | CUR-2072 | +C*+G*+G*T*T*G*C*A*T*G*A*A*G*+G*+C*+G |
| SEQ ID NO: 39 | CUR-2073 | +T*+G*+G*C*T*G*G*C*G*A*T*T*C*+A*+T*+A |
| SEQ ID NO: 40 | CUR-2074 | +C*+A*+A*C*A*T*A*T*C*A*G*G*A*+G*+C*+C |
| SEQ ID NO: 41 | CUR-2075 | +T*+G*+T*A*T*T*C*C*C*A*G*A*A*+C*+T*+T |
| SEQ ID NO: 42 | CUR-2076 (Antisense) | rUrArUrGrGrUrUrArUrUrCrArUrArCrUrUrCrGrGrUrUrGrCrArUrG |
| SEQ ID NO: 43 | CUR-2077 (Antisense) | rArGrArArGrUrArArArCrGrUrCrArCrGrGrArCrArArGrGrCrArArC |
| SEQ ID NO: 44 | CUR-2078 (Antisense) | rArUrUrUrCrUrArCrGrArGrArCrCrArArArGrUrGrUrArArUrCrCrCrArU |
| SEQ ID NO: 45 | CUR-2079 (Antisense) | rUrArArGrGrArCrGrCrGrGrArCrUrUrGrUrArCrArCrUrUrCrCrGrGrG |
| SEQ ID NO: 46 | CUR-2080 (Antisense) | rArGrArArArGrArArArGrUrUrCrUrArArCrCrUrGrUrCrUrGrUrGrU |
| SEQ ID NO: 47 | CUR-2081 | +G*+A*+T*T*T*C*A*G*A*G*C*C*G*+C*+A*+G |
| SEQ ID NO: 48 | CUR-2082 | +G*+A*+C*A*C*A*T*C*C*A*T*C*C*+C*+A*+G |
| SEQ ID NO: 49 | CUR-2083 | +C*+C*+T*C*G*T*C*A*T*G*T*C*T*+G*+T*+G |
| SEQ ID NO: 50 | CUR-0071 | C*+T*+T*G*A*A*T*T*G*T*T*T*+G*+T*+A |
| SEQ ID NO: 51 | CUR-0072 | A*+G*+T*T*G*C*A*A*G*A*G*T*+T*+G*+G |
| SEQ ID NO: 52 | CUR-0073 | A*+T*+C*T*G*T*T*C*T*G*C*T*+G*+T*+C |
| SEQ ID NO: 53 | CUR-0074 | C*+A*+T*A*T*T*C*T*T*G*G*A*+C*+G*+A |
| SEQ ID NO: 54 | CUR-0075 | T*+G*+T*G*C*T*G*T*T*G*T*A*+A*+G*+A |

TABLE 1-continued

| Sequence ID | Antisense Sequence Name | Sequence |
|---|---|---|
| SEQ ID NO: 55 | CUR-0076 | T*+G*+A*C*A*G*A*G*G*A*G*T*+A*+T*+T |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease. Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In an embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In an embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In an embodiment, the antisense oligonucleotides, such as for example, nucleic acid molecules set forth in SEQ ID NOS: 12 to 49 comprise one or more substitutions or modifications. In one embodiment, the nucleotides are substituted with locked nucleic acids (LNA).

In an embodiment, the oligonucleotides target one or more regions of the nucleic acid molecules sense and/or antisense of coding and/or non-coding sequences associated with BDNF and the sequences set forth as SEQ ID NOS: 1 to 11. The oligonucleotides are also targeted to overlapping regions of SEQ ID NOS: 1 to 11.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one an embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In an embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other an embodiment, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In an embodiment, the chimeric oligonucleotide is also modified to enhance nuclease resistance. Cells contain a variety of exo- and endonucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH,). The amide backbones disclosed by De Mesmaeker et al. (1995) Acc. Chem. Res. 28:366-374 are also preferred. Also preferred are oligonucleotides having morpholino backbone structures (Summerton and Weller, U.S. Pat. No. 5,034,506). In other an embodiment, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. Preferred oligonucleotides comprise one of the following at the 2' position: OH, SH, SCH3, F, OCN, OCH3, O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)]. Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyamine or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In an embodiment of the invention the oligonucleotides with phosphorothioate backbones and oligonucleosides with heteroatom backbones, and in particular—CH2-NH—O—CH2-, —CH2-N(CH3)-O—CH2-known as a methylene (methylimino) or MMI backbone, —CH2-O—N(CH3)-CH2-, —CH2N(CH3)-N(CH3)CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to C0 alkyl or $C_2$ to $C_{10}$ alkenyl and alkynyl. Particularly preferred are O(CH2)n OmCH3, O(CH2)n, OCH3, O(CH2)nNH2, O(CH2)nCH3, O(CH2)nONH2, and O(CH2)nON(CH3)2 where n and m can be from 1 to about 10. Other preferred oligonucleotides comprise one of the following at the 2' position: C to C0, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O-CH2-O—CH2-N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and O-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486, 603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships that exist between Brain derived neurotrophic factor (BDNF) polynucleotides and a disease state, phenotype, or condition. These methods include detecting or modulating BDNF polynucleotides comprising contacting a sample, tissue, cell, or organism with the compounds of the present invention, measuring the nucleic acid or protein level of BDNF polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

BDNF protein and mRNA expression can be assayed using methods known to those of skill in the art and described elsewhere herein. For example, immunoassays such as the ELISA can be used to measure protein levels. BDNF ELISA assay kits are available commercially, e.g., from R&D Systems (Minneapolis, Minn.).

In embodiments, BDNF expression (e.g., mRNA or protein) in a sample (e.g., cells or tissues in vivo or in vitro) treated using an antisense oligonucleotide of the invention is evaluated by comparison with BDNF expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the BDNF protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of BDNF mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of BDNF mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Brain derived neurotrophic factor (BDNF) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

The compounds of the invention are useful for research and diagnostics, because these compounds hybridize to nucleic acids encoding Brain derived neurotrophic factor (BDNF). For example, oligonucleotides that hybridize with such efficiency and under such conditions as disclosed herein as to be effective BDNF modulators are effective primers or probes under conditions favoring gene amplification or detection, respectively. These primers and probes are useful in methods requiring the specific detection of nucleic acid molecules encoding BDNF and in the amplification of said nucleic acid molecules for detection or for use in further studies of BDNF. Hybridization of the antisense oligonucleotides, particularly the primers and probes, of the invention with a nucleic acid encoding BDNF can be detected by means known in the art. Such means may include conjugation of an enzyme to the oligonucleotide, radiolabeling of the oligonucleotide, or any other suitable detection means. Kits using such detection means for detecting the level of BDNF in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of BDNF polynucleotides is treated by administering antisense compounds in accordance with this invention. For example, in one non-limiting embodiment, the methods comprise the step of administering to the animal in need of treatment, a therapeutically effective amount of BDNF modulator. The BDNF modulators of the present invention effectively modulate the activity of the BDNF or modulate the expression of the BDNF protein. In one embodiment, the activity or expression of BDNF in an animal is inhibited by about 10% as compared to a control. Preferably, the activity or expression of BDNF in an animal is inhibited by about 30%. More preferably, the activity or expression of BDNF in an animal is inhibited by 50% or more. Thus, the oligomeric compounds modulate expression of Brain derived neurotrophic factor (BDNF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Brain derived neurotrophic factor (BDNF) in an animal is increased by about 10% as compared to a control. Preferably, the activity or expression of BDNF in an animal is increased by about 30%. More preferably, the activity or expression of BDNF in an animal is increased by 50% or more. Thus, the oligomeric compounds modulate expression of BDNF mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the increase or reduction of the expression of Brain derived neurotrophic factor (BDNF) may be measured in serum, blood, adipose tissue, liver or any other body fluid, tissue or organ of the animal. Preferably, the cells contained within said fluids, tissues or organs being analyzed contain a nucleic acid molecule encoding BDNF peptides and/or the BDNF protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H phosphonate, a polyamine or a polyethylene glycol chain, or Adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 12 to 49) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adeno-viral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoyl-phosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexyl-nitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Brain derived neurotrophic factor (BDNF), and the second target may be a region from another nucleotide sequence. Alternatively, compositions of the invention may contain two or more antisense compounds targeted to different regions of the same Brain derived neurotrophic factor (BDNF) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in vitro and in vivo animal models. In general, dosage is from 0.01 µg to 10 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 10 mg per kg of body weight, once or more daily, to once every 2-20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 10 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to a Brain Derived Neurotrophic Factor (BDNF) and/or a Sense Strand of BDNF Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs (e.g. IDT AntiSense Design, IDT OligoAnalyzer) that automatically identify in each given sequence subsequences of 19-25 nucleotides that will form hybrids with a target polynucleotide sequence with a desired melting temperature (usually 50-60° C.) and will not form self-dimers or other complex secondary structures.

Selection of appropriate oligonucleotides is further facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of genes and intergenic regions of a given genome allows the selection of nucleic acid sequences that display an appropriate degree of specificity to the gene of interest. These procedures allow the selection of oligonucleotides that exhibit a high degree of complementarity to target nucleic acid sequences and a lower degree of complementarity to other nucleic acid sequences in a given genome. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or light-Typer instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example lightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Design of Modified AntagoNAT Molecules:

A number of DNA based antisense oligonucleotides were designed and tested, termed AntagoNATs, targeting noncoding Bdnf-AS and other antisense transcripts. Various AntagoNATs were designed ranging from 12 to 20 nucleotides in length with or without full phosphorothioate modification plus/minus 2-O'-methyl RNA or LNA modified nucleotides. highest efficacy was observed on Bdnf mRNA level with 16-nucleotide phosphorothioate gapmer with three LNA-modified nucleotides at each end (XXX-nnnnnnnnnnXXX). For blocking interactions between human BDNF sense-antisense transcripts, 14-nucleotide mixmers containing both LNA and 2-0'-methyl RNA molecules were used. Although these 2-0'-methyl RNA-modified oligonucleotides are suggested to only block the RNA, marginal downregulation of targeted RNAs was observed in this experiment (FIG. 11). Sequences of various AntagoNATs, as well as all other siRNAs, primers and probes used for these studies are listed in Table 1.

Example 2: Modulation of BDNF Polynucleotides

All antisense oligonucleotides used in Example 2 were designed as described in Example 1. The manufacturer (IDT Inc. of Coralville, Iowa) was instructed to manufacture the designed phosphothioate bond oligonucleotides and provided the designed phosphothioate analogs shown in Table 1. The asterisk designation between nucleotides indicates the presence of phosphothioate bond. The oligonucleotides required for the experiment in Example 2 can be synthesized using any appropriate state of the art method, for example the method used by IDT: on solid support, such as a 5 micron controlled pore glass bead (CPG), using phosphoramidite monomers (normal nucleotides with all active groups protected with protection groups, e.g. trityl group on sugar, benzoyl on A and C and N-2-isobutyryl on G). Protection groups prevent the unwanted reactions during oligonucleotide synthesis. Protection groups are removed at the end of the synthesis process. The initial nucleotide is linked to the solid support through the 3'carbon and the synthesis proceeds in the 3' to 5' direction. The addition of a new base to a growing oligonucleotide chain takes place in four steps: 1)

the protection group is removed from the 5' oxygen of the immobilized nucleotide using trichloroacetic acid; 2) the immobilized and the next-in-sequence nucleotides are coupled together using tetrazole; the reaction proceeds through a tetrazolyl phosphoramidite intermediate; 3) the unreacted free nucleotides and reaction byproducts are washed away and the unreacted immobilized oligonucleotides are capped to prevent their participation in the next round of synthesis; capping is achieved by acetylating the free 5' hydroxyl using acetic anhydride and N-methyl imidazole; 4) to stabilize the bond between the nucleotides the phosphorus is oxidized using iodine and water, if a phosphodiester bond is to be produced, or Beaucage reagent (3H-1,2-benzodithiol-3-one-1,1-dioxide), if a phosphothioate bond is desired. By alternating the two oxidizing agents, a chimeric backbone can be constructed. The four step cycle described above is repeated for every nucleotide in the sequence. When the complete sequence is synthesized, the oligonucleotide is cleaved from the solid support and deprotected using ammonium hydroxide at high temperature. Protection groups are washed away by desalting and the remaining oligonucleotides are lyophilized.

Treatment of Hek293 Cells with Different siRNA to Quantify the Amount of BDNF mRNA 1. Hek293 cells from ATCC (cat# CRL-1573) were grown in MEM/EBSS (Hyclone cat #SH30024)+10% FBS+penicillin+streptomycin at 37° C. and 5% $CO_2$. One day before the experiment the cells were replated at the density of $5 \times 10^5$/well into 6 well plates and incubated at 37° C. and 5% $CO_2$.

2. On the day of the experiment the media in the 6 well plates was changed to fresh MEM/EBSS+10% FBS.

3. All BDNF-AntagoNAT (oligonucleotide antisense of BDNF-AS) were diluted to the concentration of 20 uM and the BDNF-AS siRNA (siRNA complementary of BDNF-AS at 10 uM; both oligonucleotide compounds are manufactured by IDT. To dose one well, 2 µl of this solution was incubated with 400 µl of Opti-MEM media (Gibco cat#31985-070) and 4 ul of Lipofectamine 2000 (Invitrogen cat#11668019) at room temperature for 20 min and applied drop wise to one well of the 6 well plates with HepG2 cells. Similar mixture including 2 µl of water instead of the oligonucleotide solution was used for the mock-transfected controls.

4. After 3-18 h of incubation at 37° C. and 5% $CO_2$ the media was changed to fresh MEM/EBSS+10% FBS+penicillin+streptomycin.

5. 48 h after addition of antisense oligonuclotides was performed. The media was then removed and RNA was extracted from the cells using SV Total RNA Isolation System from Promega (cat # Z3105) or RNeasy Total RNA Isolation kit from Qiagen (cat#74181) following the manufacturers' instructions.

6. 200-400 ng of extracted RNA was added to the reverse transcription reaction performed using random hexamers, 2.5 mM mixture of dNTP, $MgCl_2$ and appropriate buffer. The cDNA (20-40 ng) from this reverse transcription reaction was used to monitor gene expression by real time PCR using ABI Taqman Gene Expression Mix (cat#4369510) and 300 nM of forward and reverse primers, and 200 nM of probe in a final reaction volume of 15 µl. The primers/probes were designed using FileBuilder software (Applied Biosystem). Primers were strand specific for sense-antisense pairs and the probes covered exon boundaries to eliminate the chance of genomic DNA amplification. The ABI assay for human BDNF was Applied Biosystems Taqman Gene Expression Assay: Hs00542425_s1 (BDNF) by Applied Biosystems Inc., Foster City Calif.). The following PCR cycle was used: 50° C. for 2 min, 95° C. for 10 min, 40 cycles of (95° C. for 15 seconds, 60° C. for 1 min) using GeneAmp 7900 Machine (Applied Biosystems). Fold change in gene expression after treatment with antisense oligonucleotides was calculated based on the difference in 18S-normalized dCt values between treated and mock-transfected samples.

7. Detection oligos for BDNF-AS:
ABI assay ID Hs00417345_m1
Context sequence GCACACCTGGAGATACTCTATTATA (SEQ ID No.: 65)

8. Detection oligos for BDNF:
ABI assay ID Hs00542425_s1
CCTGCAGAATGGCCTGGAATTACAA (SEQ ID No.: 66)
Detection oligos for BDNF-AS: ABI assay ID Hs00417345_m1
Context sequence GCACACCTGGAGATACTCTATTATA (SEQ ID No.: 65)
Detection oligos for BDNF: ABI assay ID Hs00542425_s1
CCTGCAGAATGGCCTGGAATTACAA (SEQ ID No.: 66)

9. The results are based on cycle threshold (Ct) values. The calculated differences between the Ct values for experimental and references genes (18S RNA) as ddCt and graphed as a percentage of each RNA to calibrator sample.

Results:

Transfection of several human and mouse cells lines including HEK293T cells with different siRNA that target non-overlapping regions of the BDNF-AS transcript show a 2-6 fold upregulation of the BDNF transcript (FIG. 1A and FIG. 6) at 48h. The up-regulation of BDNF was not related to the choice of endogenous controls (FIGS. 5A and 5B). The up-regulation of did not affect the regulation of other BDNF neighboring genes (FIG. 9).

FIGS. 5A and 5B show BDNF-AS knockdown leads to BDNF mRNA upregulation. Knockdown of BDNF-AS, using siRNAs-1 (10 nM) targeting the non-overlapping region of the BDNF-AS transcript, caused a 6-fold upregulation of BDNF (sense) mRNA (****=P<0.0001). Results depicted here were obtained from experiments in HEK293T cells, using beta actin (left panel) or 18S rRNA (right panel) as endogenous controls and the mock transfection as a reference sample. This experiment is intended to show that choice of endogenous controls or reference calibrator sample does not change the observed upregulation of BDNF mRNA.

FIG. 6 shows Posttranscriptional regulation of Bdnf expression. Transfected N2a cells with combination of mBdnf-AntagoNAT9 targeting mouse Bdnf-AS transcript and Drosha siRNA targeting Drosha protein, which is involved in microRNA (miRNA) processing. Bdnf mRNA upregulation was observed following treatment of cells with mBdnf-ANtagoNAT9 (***=p value<0.0001). Addition of Drosha siRNA marginally increased Bdnf transcript over mBdnf-AntagoNAT9 treatment (*=p value<0.05). This experiment may suggest involvement of other posttranscriptional mechanisms, such as miRNAs in regulation of Bdnf transcript.

Figure 9:
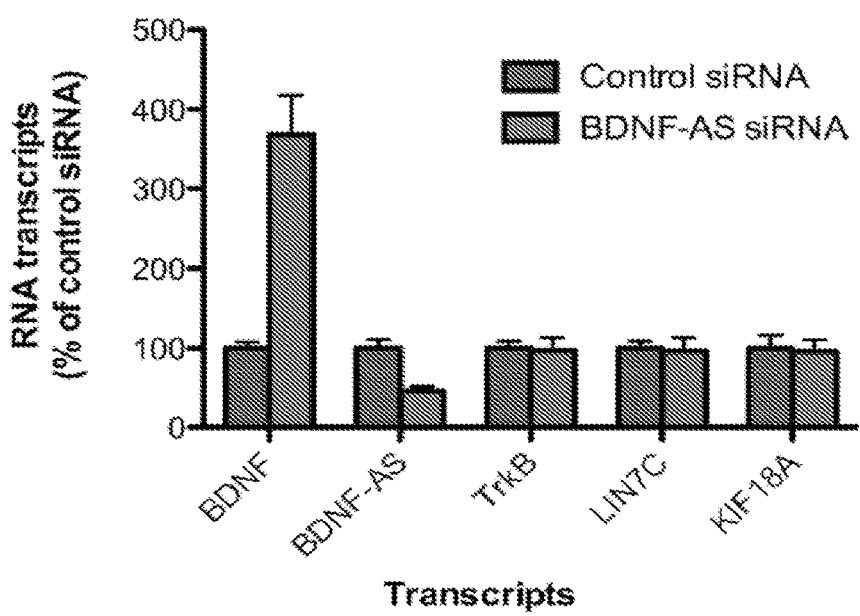
FIG. 9 shows BDNF-AS knockdown neither changes the level of TrkB nor BDNF neighboring genes (Let7C and KIF18A) in both directions: LIN7C and KIF18A are genes located 3' downstream and 5' upstream of BDNF, respectively.

FIG. 9 shows BDNF-AS knockdown neither changes the level of TrkB nor BDNF neighboring genes (Let7C and KIF18A) in both directions: LIN7C and KIF18A are genes located 3' downstream and 5' upstream of BDNF, respectively. Neurotrophic tyrosine kinase, receptor, type 2 (TrkB) encodes a membrane-bound receptor for BDNF and is located on a different chromosome (Chr-9) as BDNF. It was determined whether these genes were altered upon depletion of the BDNF-AS transcript. HEK293T cells were transfected with control siRNA or BDNF-AS siRNA and measured several transcript levels. It was observed that the BDNF-AS transcript was downregulated and that BDNF mRNA was upregulated as indicated elsewhere in this manuscript. It was found that the knockdown of BDNFAS has no effect on TrkB expression or on the neighboring genes Let7C and KIF18A. These data suggest that upon BDNF-AS depletion, there is a locus-specific alteration of BDNF expression.

Treatment of Hek293 Cells with One siRNA in a Time Course of 0-96 h to Quantify the Amount of BDNF and BDNF-AS The methodology followed was same as in Treatment of Hek293 cells with siRNA but this time the cells are harvested at 0 to 96h after addition of the oligos.

Figure 1B:
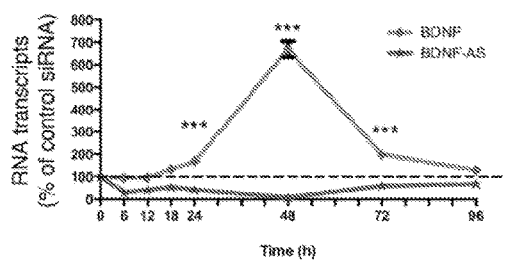

Results:

The time course of BDNF and BDNF-AS expression shows an optimum up-regulation of BDNF due to the siRNA at 48h simultaneously to an optimum downregulation of the BDNF-AS (FIG. 1B).

Treatment of Hek293 Cells with Different hBDNF-AntagoNATs to Quantify the Amount of BDNF and BDNF-AS The methodology followed was same as in Treatment of Hek293 cells with siRNA but this time the cells are treated with AntagoNATs.

Figure 7:
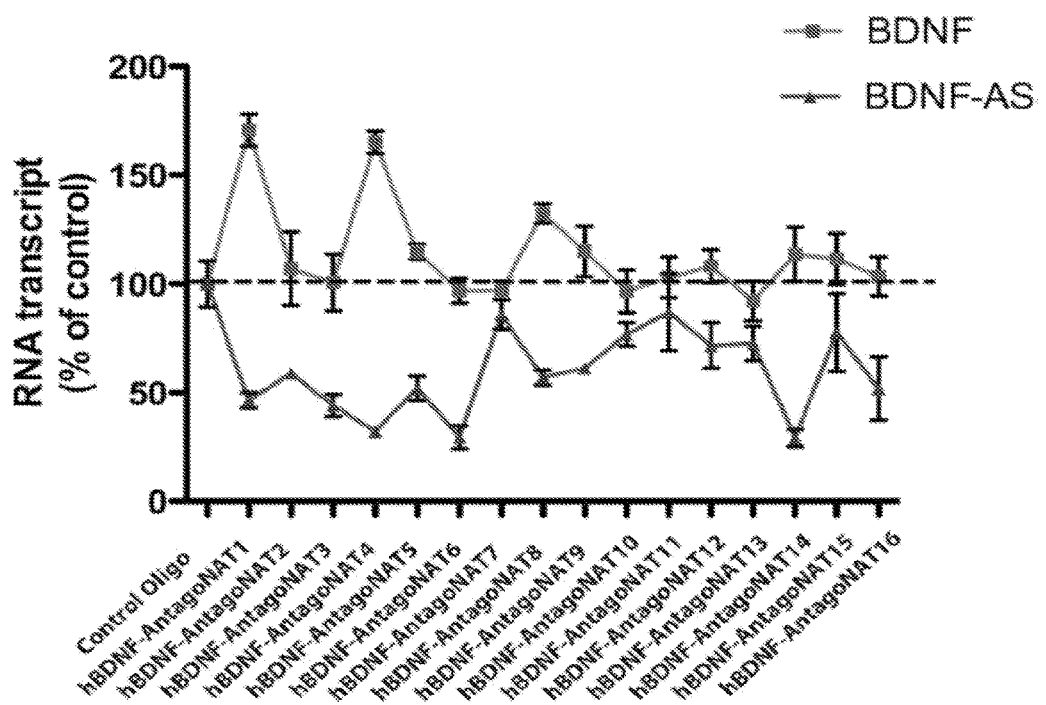
FIG. 7 shows Inhibition of the human BDNF-AS transcript by hBDNFAntagoNAT.

Results:

The BDNF-AS transcript contains a 225-nucleotide overlapping region that has full complementarity to the BDNF mRNA. TheRNA-RNA interactions may be responsible for the discordant regulation of BDNF by its antisense transcript. To determine the regulatory role of BDNF-AS on BDNF mRNA, the gapmers (AntagoNATs) containing both LNA and 2'OMe RNA modifications were utilized to block the interaction between sense and antisense transcripts. The overlapping region was covered by tiling hBDNF-AatagoNATs. It was found that the use of hBDNF-AntagoNATs upregulates the BDNF mRNA. A marginal downregulation of BDNF-AS transcript was observed, which was not expected for 2'OMe-RNA containing blocking oligos. The 16 hBDNF-AntagoNATs were tested and it was found that blocking the first half of the BDNF-AS overlapping region has a greater effect on the upregulation of BDNF mRNA. Specifically, hBDNF-AntagoNAT1 and hBDNFAntagoNAT4 caused significant upregulation of BDNF mRNA. Unlike synthetic siRNAs, antisense oligonucleotides are single-stranded and can be shorter in length; therefore, reducing non-specific (off-target) binding effects. Single-stranded locked nucleic acid (LNA)-modified oligonucleotides are generally more effective, in vivo, compared to unmodified siRNAs (FIG. 7).

Treatment of Mouse N2a Cells with Different mBDNF-AntagoNATs to Quantify the Amount of BDNF and BDNF-AS The methodology followed was same as in Treatment of Hek293 cells with different hBDNF-AntagoNATs to quantify the amount of BDNF and BDNF-AS but this time the cells are N2a cells. Furthermore, the following PCR cycle was used: 50° C. for 2 min, 95° C. for 10 min, 50 cycles of (95° C. for 15 seconds, 60° C. for 1 min) using GeneAmp 7900 Machine (Applied Biosystems).

Figure 8:
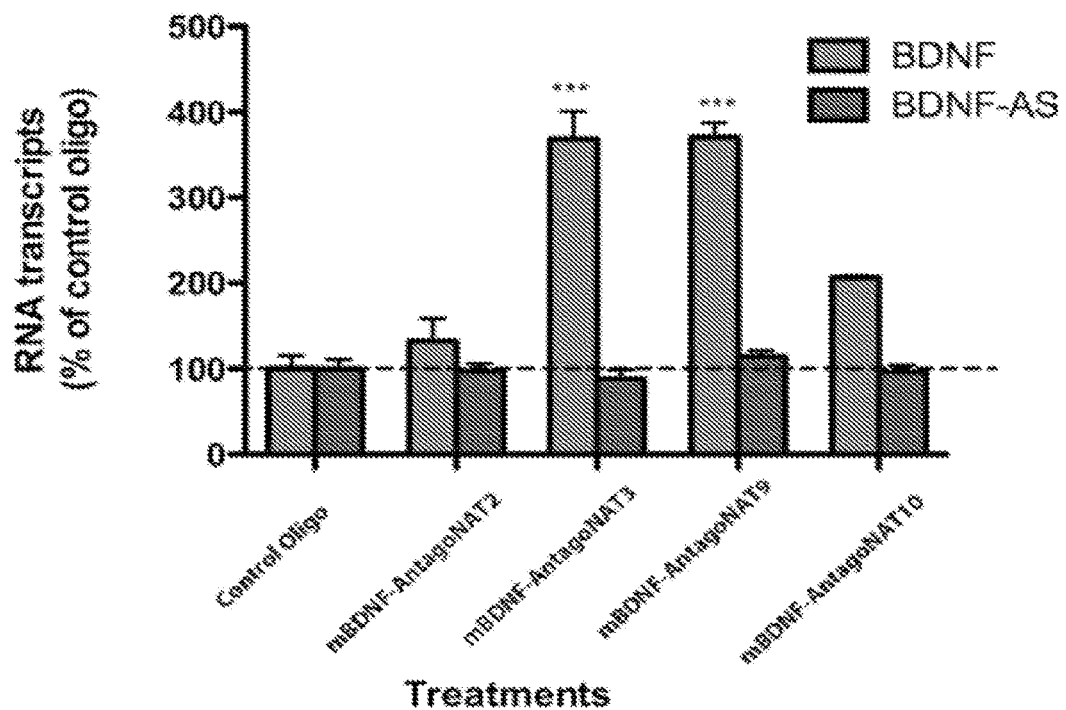
FIG. 8 shows Inhibition of the mouse BDNF-AS transcript in N2a cells, by AntagoNATs.

Results:

FIG. 8 shows Inhibition of the mouse Bdnf-AS transcript in N2a cells, by AntagoNATs: that blocking of the overlap region between human BDNF sense and antisense transcripts upregulates BDNF mRNA levels. It was then determined if a similar regulatory mechanism exists in a mouse cell line and tested 11 mBdnf-AntagoNATs that target the mouse Bdnf-AS transcript. mBdnf-AntagoNATs contain a phosphorothioate backbone and three LNA-modified nucleotides at both 3' and 5' ends. Control oligonucleotides have a similar backbone and modifications, but do not target any sequence in the mammalian genomes. Two mBdnf-AntagoNATs (mBdnf-AntagoNA3 and mBdnf-AntagoNAT-9) were able to increase Bdnf mRNA levels in N2a cells. In sum, blocking the mouse Bdnf-AS transcript with single-stranded AntagoNATs (16-mer) caused an upregulation of Bdnf mRNA levels in mouse N2a cells. These data suggest that the antisense transcript of Bdnf exerts a suppressive effect on Bdnf mRNA.

Treatment of Hek293 Cells with Different siRNA to Quantify the BDNF Protein

Figure 1C:
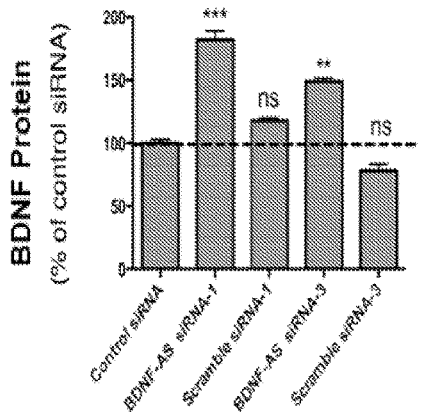
Figure 1D:
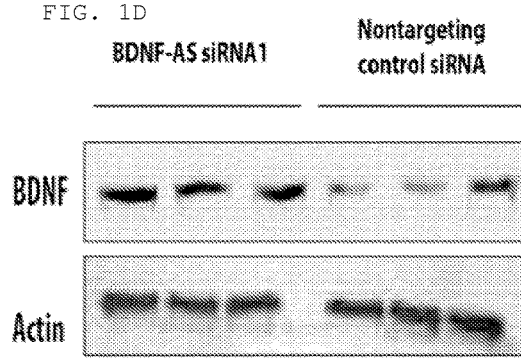

The methodology followed was same as in Treatment of Hek293 cells with different siRNA to quantify the amount of BDNF mRNA, except at step 5 where, 48h after addition of siRNA was performed. The media was then removed and cells were disrupted and their levels of BDNF protein was quantified by ELISA (FIG. 1C) and western blot (FIG. 1D).

Western Blot:

HEK293T cells were transfected with 10 nM of BDNF-AS, or control siRNA. The cells were disrupted, 48 h post transfection, with 200 μl of Laemmli sample buffer (Biorad) containing 350 mM DTT. 20 μl of the lysate was separated on a 10% SDS PAGE and transferred it to a nitrocellulose membrane overnight. Then the incubated the membrane with primary antibody for MecP2 (Abcam), BDNF (Promega, catalog number G164B) and secondary antibody conjugated to HRP. After addition of HRP substrate, the chemiluminescent signal was detected with X-ray film. The same membrane was stripped and reused it for detection of (3-Actin as a loading control.

ELISA:

Cells were transfected with 20 nM of BDNF-AS siRNA or control siRNA. The cell supernatant was collected for ELISA experiments. Alternatively, total protein was extracted from mouse brain tissues embedded in protein extraction buffer plus protease inhibitors (BCA kit, Fisher) and homogenized with the bioruptor and metal beads. Total protein was measured using BCA protein assay kit (Pierce catalog number 23227) and sample loads were normalized to total protein concentrations. the ELISA kits were purchased for human BDNF from Promega (catalog number G7611) or mouse Bdnf Millipore (catalog number CYT306) and ELISA was performed following the supplier's protocol. Average absorbance was subtracted of three repeats at 450 nm from background and normalized it to the control sample.

Treatment of Hek293 Cells with Different Concentrations of mBDNF-AntagoNAT9 to Quantify the BDNF mRNA The methodology followed was same as in Treatment of Hek293 cells with different siRNA to quantify the amount of BDNF mRNA except at step 3, where all mBDNF-AntagoNAT9 was diluted to different concentration such as the final of 11 different concentrations were applied to the cells (1:3 serial dilutions ranging from 300 nM to 5 pM) using the same proportional amounts of Lipofectamine 2000 (Invitrogen cat#11668019) as in Treatment of Hek293 cells with different siRNA to quantify the amount of BDNF mRNA, using the in a same volume of Opti-MEM media (Gibco cat#31985-070). This was performed at room temperature for 20 min and applied dropwise to one well of the 6 well plates with HepG2 cells. Similar mixture including water instead of the oligonucleotide solution was used for the mock-transfected controls.

Figure 1E:
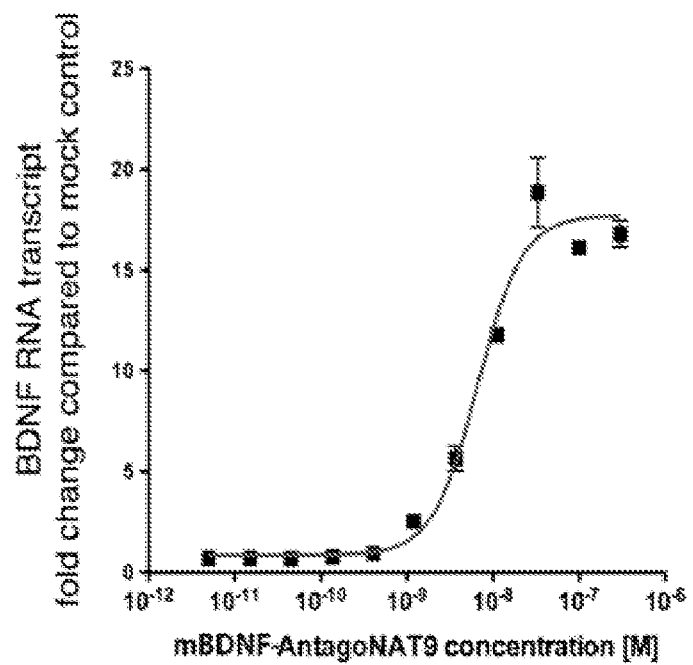
Figure 2A:
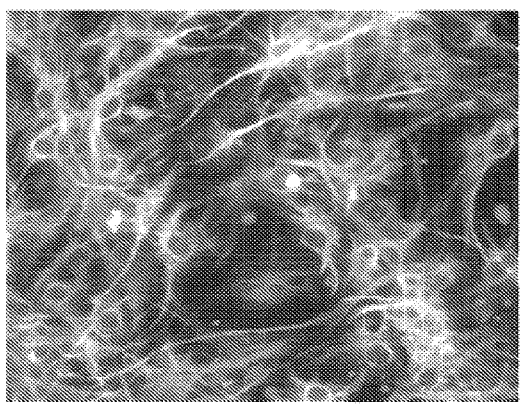
FIG. 2A-2D shows BDNF upregulation increases neuronal outgrowth.
Figure 2B:
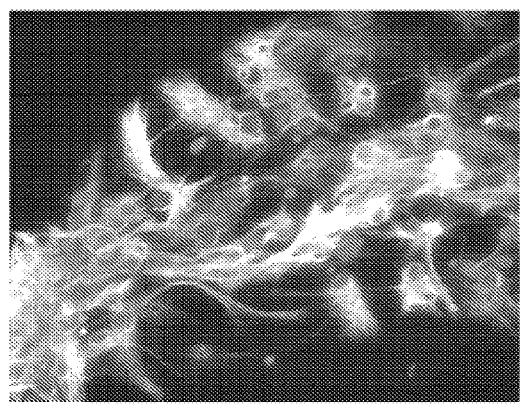
Figure 2C:
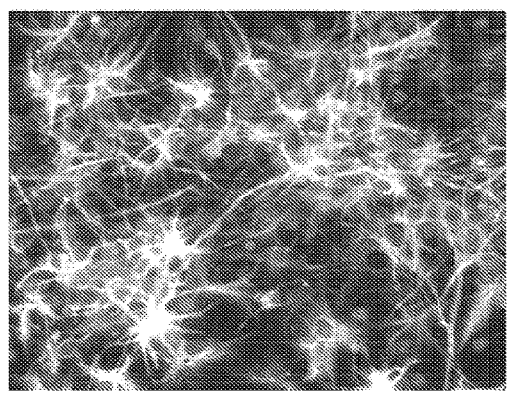
Figure 2D:
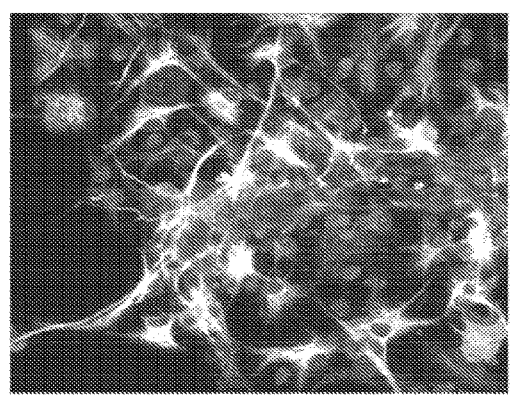

Results:

As shown here in FIG. 1E, there is a dose-dependent up-regulation of BDNF when BDNF-AS is targeted by mBDNF-AntagoNAT9.

FIGS. 1A to 1E show antisense-mediated regulation of sense mRNA and protein. (FIG. 1A) Knockdown of brain derived neurotrophic factor (BDNF) natural antisense transcript, BDNF-AS, in HEK293T cells (n=12 per treatment) with each of three unique siRNAs (10 nM) targeting the non-overlapping region of BDNF-AS transcript, caused 2-6 fold upregulation of BDNF (sense) mRNA (n=6 for each data point/treatment *=P<0.001, =P<0.01). Similar results were obtained from experiments using Human cortical neuron (HCN), glioblastoma (MK059) cells, mouse N2a cells and neurospheres "data not shown". Scrambled sequences, mock transfection and control siRNAs were used as controls. Control siRNA for this and other experiments is an inert siRNA (CCUCUCCACGCGCAGUACATT (SEQ ID NO: 67)) that does not target any known sequence in the mammalian genome. All measurements were normalized to the 18S rRNA and graphed as a percentage of each mRNA to the negative siRNA control sample.

(FIG. 1B) Changes in BDNF and BDNF-AS transcripts were assessed over a period of time, following BDNF-AS knockdown (n=6 for each data point/treatment). siRNA knockdown of human BDNF-AS resulted in efficient and consistent downregulation of BDNF-AS, starting at 6 h and continuing on to 72 h. BDNF mRNA levels rose at 18 h, remaining high for more than 72 h, reversing to pre-treatment levels at 96 h. Note that the peak at 48 h is consistent and reproducible. Although BDNF-AS knockdown begins after 6 h, upregulation of BDNF started 18 h post-treatment. This time lag between the depletion of BDNF-AS and the increase of BDNF mRNA shows the sequential order of events indicating that the cells require time to adapt to the removal of the antisense transcript before upregulating BDNF.

(FIG. 1C) siRNA-mediated knockdown of BDNF-AS transcript caused an increase in BDNF protein levels measured by ELISA. Cells were transfected with 10 nM of two active siRNAs for BDNF-AS, scrambled siRNAs or a control siRNA for 48 hours. The supernatants of these cells were concentrated and analyzed for BDNF protein by ELISA, using a commercially available kit. BDNF protein was significantly increased (n=6 per treatment, *=P<0.0001, =P<0.001) with siRNA targeting BDNF-AS transcript.

(FIG. 1D) Western blots confirmed that knockdown of the non-protein-coding BDNF-AS, with BDNF-AS siRNA1, but control non-targeting siRNA transcript increased BDNF protein levels without changing the levels of beta-actin. Collectively, these data suggest that there is a discordant relationship between the sense and antisense BDNF transcripts in which BDNF-AS suppresses the expression of BDNF mRNA and protein. Removal of this negative regulatory effect, by BDNF-AS knockdown, causes upregulation of BDNF mRNA and protein levels.

(FIG. 1E) Dose-dependent increases in Bdnf following Bdnf-AS depletion: dose response experiments were performed using 11 different concentrations (1:3 serial dilutions ranging from 300 nM to 5 pM) of mBdnf-AntagoNAT9 (n=6 per data point/treatment) and a dose-dependent increase was observed in Bdnf mRNA levels at 1-300 nM concentration with an EC50 of 6.6 nM.

Treatment of Hippocampal Neurospheres with siRNA
Dissecting Mouse Hippocampal Neural Stem Cells in Neurospheres:

neuronal stem cells were separated from the hippocampus of mouse pups, P0-P1. The hippocampi were mechanically separated to single cells, collected by short spins and grown in a mixture of DMEM and F12, containing glutamine, antibiotics, B27 solution and 0.001 mM concentration of both EGF and FGF. After 3-4 days floating neurospheres formed. 100,000 cells were plated in 24-well plates coated with poly-L-Lysine (PLL). The plating of neurosphere cells onto PLL will start the differentiation process. On the third day post-plating, growth factors were removed from the medium and allowed the cells to grow for 4 more days (7 days post-plating). By this time, the cell culture had a mix of neural cell lineages consisting of astrocytes, neurons, oligodendrocytes and their progenitors making it more similar to mature brain tissue. The expression of BDNF and BDNF-AS was measured in floating neurospheres as well as in 3 and 7 days post-plating cultures. Knockdown experiments were performed, using either 50 nM siRNAs or 20 nM antisense oligonucleotides targeting BDNF-AS transcript, at 3 or 7 days post-plating. Neural stem cells were also seeded in immunocytochemistry chambers, (18,000 cell per well) in a total volume of 80 µl. Neurospheres were then transfected, using the same protocol, to assess the functional effects of BDNF-AS knockdown on murine primary cells. After 48-72 h, cells were fixed with paraformaldehyde (4%) for 20 min and washed with 1×PBS several times. After blocking with FBS, neurospheres were incubated with primary antibody (Monoclonal Rabbit β tubulin III, TUJ1) at a 1:2000 concentration overnight. Fixed cells were incubated with secondary antibody, labeled with Alexafluor 568 (goat anti-rabbit IgG, 2 mg/ml, at concentration of 1:5000). Nuclei were stained with Hoechst stain. Images were obtained by immunofluorescence antigen detection microscopy.

Targeting of BDNF-AS by AntagoNATs:

The term AntagoNAT is used here to describe single-stranded oligonucleotide molecules that inhibit sense-antisense interactions (with different modifications, see supplementary methods). Single-stranded gapmer were designed, oligonucleotides, 14 nucleotides in length, with 2'O-Methyl RNA and/or locked nucleic acid (LNA) modifications. Using this strategy, we tiled the entire overlapping region between human BDNF-AS and BDNF transcripts and identified several efficacious AntagoNATs capable of upregulating of BDNF mRNA. hBDNF-AntagoNAT1 and hBDNF-AntagoNAT4, targeting the first part of the overlapping region, produced the largest response. The data suggests that blockage of BDNF antisense RNA, by single-stranded AntagoNATs, is sufficient in causing an increase in BDNF mRNA.

Then single-stranded gapmers were designed: LNA-modified, 15 DNA oligonucleotides (AntagoNATs) 16-nucleotides in length with phosphorothioate backbone, complementary to mouse Bdnf-AS. Two AntagoNATs (mBdnf-AntagoNAT3 and mBdnf-AntagoNAT9) consistently showed a statistically significant increase in Bdnf mRNA levels in mouse N2a cells (FIG. 8).

FIG. 7 shows Inhibition of the human BDNF-AS transcript by hBDNFAntagoNAT: The BDNF-AS transcript contains a 225-nucleotide overlapping region that has full complementarity to the BDNF mRNA. RNA-RNA interactions may be responsible for the discordant regulation of BDNF by its antisense transcript. To determine the regulatory role of BDNF-AS on BDNF mRNA, gapmers (AntagoNATs) containing both LNA and 2'OMe RNA modification were utilized to block the interaction between sense and antisense transcripts. overlapping region was covered by tiling hBDNF-AatagoNATs. It was found that the use of hBDNF-AntagoNATs upregulates the BDNF mRNA. Marginal downregulation of BDNF-AS transcript was observed, which was not expected for 2'OMe-RNA containing blocking oligos. 16 hBDNF-AntagoNATs (14-mers each with the sequences provided below) were tested and it was found that blocking the first half of the BDNF-AS overlapping region has a greater effect on the upregulation of BDNF mRNA. Specifically, hBDNF-AntagoNAT1 and hBDNFAntagoNAT4 caused significant upregulation of BDNF mRNA. Unlike synthetic siRNAs, antisense oligonucleotides are single-stranded and can be shorter in length; therefore, reducing non-specific (off-target) binding effects. Single-stranded locked nucleic acid (LNA)-modified oligonucleotides are generally more effective, in vivo, compared to unmodified siRNAs.Bdnf upregulation increases neuronal outgrowth.

Bdnf Upregulation Increases Neuronal Outgrowth:

Consistent with many previous reports that indicate stimulatory effects of BDNF on neuronal outgrowth and adult neurogenesis 16-17, it was found that an increase in the endogenous Bdnf level due to the knockdown of BDNF-AS transcript resulted in increased neuronal cell number and in neurite outgrowth and maturation at 3 and 7 days postplating in neurospheres (FIG. 4A-4E). These data suggest that the upregulation of endogenous BDNF, due to inhibition of antisense RNA, induces neuronal differentiation in neuronal progenitor cells and might cause a mature phenotype in nascent neurons.

Results:

FIG. 2 shows Bdnf upregulation increases neuronal outgrowth (FIGS. 2A and 2B) Immunocytochemistry images of hippocampal neurospheres treated with either control siRNA (FIG. 2A) or Bdnf-AS siRNA (FIG. 2B) 3 d postplating. (FIGS. 2C and 2D) Immunocytochemistry images of neuronal maturation and neurite outgrowth in hippocampal neurospheres treated with either control siRNA (FIG. 2C) or Bdnf-AS siRNA (FIG. 2D) 7 d post-plating. Treatment of cells with siRNA targeting the Bdnf-AS transcript resulted in increased neuronal cell number as well as increase in neurite outgrowth and maturation, both at 3 d or 7 d postplating neurospheres. B-tubulin III stained red, GFAP stained green and DAPI stained blue.

Delivery Intracerebroventicular (ICV) of mBDNF-AntagoNAT9 Using Osmotic Mini-Pumps Knockdown BDNF-AS and Up-Regulate BDNF Mouse Studies:

10 eight-week-old male C57BL/6 mice were used for in vivo experiments. The mice were prepared with chronic indwelling cannulae in the dorsal third ventricle implanted subcutaneously with osmotic mini-pumps that delivered continuous infusions (0.11 microliter/h) of synthetic antisense oligonucleotide directed against Bdnf-AS (mBdnf-AntagoNAT9) or control oligonucleotide (inert sequence that does not exist in human or mouse) at a dose of 1.5 mg/kg/d for 4 weeks. Tubing was connected to the exit port of the osmotic minipump and tunneled subcutaneously to the indwelling cannula, such that the treatments were delivered directly into the brain. At 5 d post-implantation all animals received daily intra-peritoneal (IP) injection of BrdU (80 mg/kg), for five consecutive days. At the 28th day post-surgery, the animals were sacrificed and three tissues were excised (hippocampus, frontal cortex and cerebellum) from each mouse brain for quantitative RNA measurements.

Knockdown of Bdnf-AS Increases Bdnf In Vivo:

Osmotic mini-pumps for intracerebroventricular (ICV) delivery of mBdnf-AntagoNAT9 to C57BL/6 mice were utilized. mBdnf-AntagoNAT9 were then selected, which is targeting a non-overlapping region of mouse Bdnf-AS, over other active AntagoNATs, based on its high efficacy to increase in Bdnf mRNA in vitro. After 28 days of continuous AntagoNAT infusion, Bdnf mRNA levels were increased across forebrain regions adjacent to the third ventricle in mice treated with mBdnf-AntagoNAT9 as compared to levels unaltered by an inert control oligonucleotide (FIGS. 3A and 3B). Bdnf and Bdnf-AS transcripts were unaltered in the hypothalamus, a structure that is not immediately adjacent to the third ventricle (FIG. 3C). Moreover, it was found that AntagoNAT-mediated blockade of Bdnf-AS results increased Bdnf protein levels (FIGS. 3D and 3E). These findings correspond with the in vitro data described above and indicate that the blockade of Bdnf-AS results in the increase of Bdnf mRNA and protein expression in vivo.

RNA Extraction and RT-PCR of the Mouse Brain Samples:

Mice were euthanized after 28 days and the brains were excised. One hemibrain from each mouse was fixed in 4% formaldehyde overnight for histological studies. Another hemibrain was excised for RNA quantitative measurement from the hippocampus, frontal cortex and cerebellum. RNA was extracted after homogenization in Trizol reagent (Invitrogen, 15596-026) according to the manufacturer's protocol. The aqueous phase was separated and added an equal volume of 70% ethanol before passing the samples through Qiagen RNeasy columns (QIAGEN, 74106) and those RNA samples were subjected to on-column DNAse treatment for removal of DNA contamination. 400 ng of each sample was used for the first strand cDNA synthesis and RT-PCR measurements were carried out. The percentile changes were plotted in RNA levels, for individual tissues as compared to control mice, in each graph.

Results: FIG. 3 shows Bdnf-AS regulates Bdnf mRNA and protein in vivo; (FIG. 3A to 3C) Using osmotic mini-pumps, mBdnf-AntagoNAT9 (CAACATATCAGGAGCC (SEQ ID NO: 40)) or control oligonucleotide (CCACGCGCAGTACATG (SEQ ID NO: 68)) was infused constantly over a period of 28 d, into the third ventricle of mouse brain (n=5 per treatment group *=P<0.05, =P<0.01, *=P<0.001). mBdnf-AntagoNAT9 directed against Bdnf-AS but not the control oligonucleotide resulted in an increase in Bdnf levels in the hippocampus (FIG. 3A) and frontal cortex (FIG. 3B). In the hypothalamus (FIG. 3C) both transcripts were unchanged, as was expected for a tissue that is not directly connected to the third ventricle of the brain. (FIG. 3D to 3E) BDNF protein levels were assessed by ELISA and found that mBdnf-AntagoNAT9 treatment results in an increase in BDNF protein, both in the hippocampus (FIG. 3D) and frontal cortex (FIG. 3E), as compared to control oligonucleotide treated mice.

Delivery Intracerebroventicular (ICV) of mBDNF-AntagoNAT9 Using Osmotic Mini-Pumps Knockdown BDNF-AS and Up-Regulate BDNF BrdU was injected in the mice treated with mBdnf-AntagoNAT9 in the first week of the study for 5 days. After 28 days of continuous AntagoNAT infusion, histological examination of brain tissues was performed and neuronal proliferation was quantified and survival using Ki67 and BrdU markers, respectively. In mice treated with mBdnf-AntagoNAT9, an increase was observed in Ki67 positive (proliferating) cells as compared to control treated mice (FIGS. 4A and 4B). the number of Ki67 positive cells was quantified and a significant increase in cell proliferation was found in mice treated with mBdnf-AntagoNAT9 compared to control oligonucleotide (FIG. 4C). In mice treated with mBdnf-AntagoNAT9, there was a significant increase in BrdU incorporation (surviving cells) as compared to the control oligonucleotide-treated mice (FIG. 4D). There were no differences in hippocampal volume between control and mBdnf-AntagoNAT9 treated mice (FIG. 4E). These findings demonstrate that Bdnf-AS regulates Bdnf levels in vivo.

Results:

FIG. 4 shows Blocking of Bdnf-AS, in vivo, causes an increase in neuronal survival and proliferation; (FIGS. 4A-4B) mice were treated with mBdnf-AntagoNAT9 or control oligos. After 28 d of continuous mBdnf-AntagoNAT9 infusion, histological examination of brain tissues was performed, using Ki67. Ki67 is the marker of proliferating cells in hippocampus and an increase in the number of proliferating cells was observed in mice received Bdnf-AntagoNAT treatment compare to mice received control oligos. In mice treated with mBdnf-AntagoNAT9 (FIG. 4B), there was an increase in Ki67 positive cells (proliferating cells), as compared to control treated mice (FIG. 4A). (FIG. 4C) Mice treated with mBdnf-AntagoNAT9 had a significant increase in the number of Ki67 positive cells as compared to control treated mice. (FIG. 4D) In mice treated with mBdnf-AntagoNAT9, there was a significant increase in the number of surviving cells (BrdU positive) as compared to control oligonucleotide treated mice. (FIG. 4E) There were no differences in hippocampal volume between control and mBdnf-AntagoNAT9 treated mice. Together these data (n=5 per treatment group *=P<0.05, ***=P<0.001) demonstrates that Bdnf-AS regulates Bdnf levels in vivo and that blocking Bdnf sense-antisense interactions results in an increase in neuronal lineage, proliferation and survival.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of upregulating the expression of a Brain derived neurotrophic factor (BDNF) polynucleotide in a biological system comprising: contacting said system with at least one antisense oligonucleotide 10 to 30 nucleotides in length wherein said at least one antisense oligonucleotide is at least 90% complementary to and specifically hybridizes to a 10 to 30 nucleotide region of a natural antisense polynucleotide of the BDNF polynucleotide in a 225-nucleotide overlapping region of the natural antisense polynucleotide, wherein said natural antisense polynucleotide consists essentially of a sequence selected from the group consisting of: nucleotides 1 to 1279 of SEQ ID NO: 3, comprising the 225-nucleotide overlapping region at nucleotides 303 to 527, 1 to 1478 of SEQ ID NO: 4, comprising the 225-nucleotide overlapping region at nucleotides 372 to 596; 1 to 1437 of SEQ ID NO: 5, comprising the 225-nucleotide overlapping region at nucleotides 303 to 527; 1 to 2322 of SEQ ID NO: 6, comprising the 225-nucleotide overlapping region at nucleotides 372 to 596; 1 to 2036 of SEQ ID NO: 7, comprising the 225-nucleotide overlapping region at nucleotides 303 to 527; and 1 to 2364 of SEQ ID NO: 8, comprising the 225-nucleotide overlapping region at nucleotides 402 to 626; thereby upregulating the expression of the BDNF polynucleotide.

2. A method of upregulating the expression of a BDNF polynucleotide in patient cells or tissues comprising: contacting said patient cells or tissues with at least one antisense oligonucleotide 10 to 30 nucleotides in length wherein said at least one antisense oligonucleotide is at least 95% complementary to and specifically hybridizes to a 10 to 30 nucleotide region of a natural antisense polynucleotide of BDNF in a 225-nucleotide overlapping region of the natural antisense polynucleotide, wherein said natural antisense polynucleotide consists essentially of a sequence selected from the group consisting of nucleotides 1 to 1279 of SEQ ID NO: 3, comprising the 225-nucleotide overlapping region at nucleotides 303 to 527; 1 to 1478 of SEQ ID NO: 4, comprising the 225-nucleotide overlapping region at nucleotides 372 to 596; 1 to 1437 of SEQ ID NO: 5, comprising the 225-nucleotide overlapping region at nucleotides 303 to 527; 1 to 2322 of SEQ ID NO: 6, comprising the 225-nucleotide overlapping region at nucleotides 372 to 596; 1 to 2036 of SEQ ID NO: 7, comprising the 225-nucleotide overlapping region at nucleotides 303 to 527; and 1 to 2364 of SEQ ID NO: 8, comprising the 225-nucleotide overlapping region at nucleotides 402 to 626; thereby upregulating the expression of the Brain derived neurotrophic factor (BDNF) polynucleotide.

3. A method of upregulating the expression of a BDNF polynucleotide in a patient comprising: contacting said patient with at least one antisense oligonucleotide of 10 to 30 nucleotides in length that is at least 95% complementary to and specifically hybridizes to a 10 to 30 nucleotide region in a 225-nucleotide overlapping region of a natural antisense polynucleotide of the BDNF polynucleotide, wherein said natural antisense polynucleotide consists essentially of a sequence selected from the group consisting of nucleotides 1 to 1279 of SEQ ID NO: 3, comprising the 225-nucleotide overlapping region at nucleotides 303 to 527; 1 to 1478 of SEQ ID NO: 4, comprising the 225-nucleotide overlapping region at nucleotides 372 to 596; 1 to 1437 of SEQ ID NO: 5, comprising the 225-nucleotide overlapping region at nucleotides 303 to 527; 1 to 2322 of SEQ ID NO: 6, comprising the 225-nucleotide overlapping region at nucleotides 372 to 596; 1 to 2036 of SEQ ID NO: comprising the 225-nucleotide overlapping region at nucleotides 303 to 527; and 1 to 2364 of SEQ ID NO: 8, comprising the 225-nucleotide overlapping region at nucleotides 402 to 626; thereby upregulating the function of and/or the expression of the BDNF polynucleotide.

4. The method of claim 1, wherein the expression of the BDNF polynucleotide is upregulated in vivo or in vitro with respect to a mock-transfected control.

5. The method of claim 3, wherein the at least one antisense oligonucleotide targets a natural antisense polynucleotide that is antisense to coding and/or non-coding nucleic acid sequences of the BDNF polynucleotide.

6. The method of claim 3, wherein the at least one antisense oligonucleotide comprises one or more modifications selected from: at least one modified sugar moiety, at least one modified internucleoside linkage, at least one modified nucleotide, and combinations thereof.

7. The method of claim 6, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

8. The method of claim 6, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, carboxymethyl ester, and combinations thereof.

9. The method of claim 6, wherein the one or more modifications comprise at least one modified nucleotide selected from: a peptide nucleic acid (PNA), a locked nucleic acid (LNA), an arabino-nucleic acid (FANA), and combinations thereof.

10. A method of upregulating the expression of a BDNF gene in mammalian cells or tissues in vivo or in vitro comprising: contacting said cells or tissues with at least one short interfering RNA (siRNA) oligonucleotide 19 to 30 nucleotides in length, said at least one siRNA oligonucleotide being specific for a natural antisense polynucleotide of a BDNF polynucleotide in a 225-nucleotide overlapping region of the natural antisense polynucleotide, and, upregulating the expression of the BDNF gene in mammalian cells or tissues in vivo or in vitro, wherein said natural antisense polynucleotide consists essentially of a sequence selected from the group consisting of: nucleotides 1 to 1279 of SEQ ID NO: 3, comprising the 225-nucleotide overlapping region at nucleotides 303 to 527; 1 to 1478 of SEQ ID NO: 4, comprising the 225-nucleotide overlapping region at nucleotides 372 to 596; 1 to 1437 of SEQ ID NO: 5, comprising the 225-nucleotide overlapping region at nucleotides 303 to 527; 1 to 2322 of SEQ ID NO: 6, comprising the 225-nucleotide overlapping region at nucleotides 372 to 596; 1 to 2036 of SEQ ID NO: 7, comprising the 225-nucleotide overlapping region at nucleotides 303 to 527; and 1 to 2364 of SEQ ID NO: 8, comprising the 225-nucleotide overlapping region at nucleotides 402 to 626.

11. The method of claim 10, wherein said oligonucleotide has 100% complementarity to said natural antisense polynucleotide.

12. A method for targeting a natural antisense transcript (NAT) of a BDNF polynucleotide with at least one antisense oligonucleotide 10 to 30 nucleotides in length, wherein the at least one antisense oligonucleotide is at least 90% complementary to and specifically hybridizes to a 10 to 30 nucleotide region of the NAT of the BDNF polynucleotide in a 225-nucleotide overlapping region of the NAT, to upregulate the expression of the BDNF polynucleotide, comprising contacting the NAT with the antisense oligonucleotide, wherein the NAT has a sequence consisting essentially of a sequence selected from the group consisting of: nucleotides 1 to 1279 of SEQ ID NO: 3, comprising the 225-nucleotide overlapping region at nucleotides 303 to 527; 1 to 1478 of SEQ ID NO: 4, comprising the 225-nucleotide overlapping region at nucleotides 372 to 596; 1 to 1437 of SEQ ID NO: 5, comprising the 225-nucleotide overlapping region at nucleotides 303 to 527; 1 to 2322 of SEQ ID NO: 6, comprising the 225-nucleotide overlapping region at nucleotides 372 to 596; 1 to 2036 of SEQ ID NO: 7, comprising the 225-nucleotide overlapping region at nucleotides 303 to 527; and 1 to 2364 of SEQ ID NO: 8, comprising the 225-nucleotide overlapping region at nucleotides 402 to 626.

13. The method of claim 1, wherein the upregulated expression of the BDNF polynucleotide results in neuronal survival, neuronal proliferation, or both.

14. The method of claim 3, wherein the expression of the BDNF polynucleotide is upregulated in the hippocampus, the frontal cortex, or both.

15. The method of claim 1, wherein the oligonucleotide is at least 95% complementary to and specifically hybridizes to the 10-30 nucleotide region of the natural antisense polynucleotide.

16. The method of claim 1, wherein the sequence of the at least one antisense oligonucleotide comprises a sequence selected from the group consisting of the sequences set forth as SEQ ID NOS: 16-31 and 35.

17. The method of claim 16, wherein the sequence of the at least one antisense oligonucleotide comprises a sequence selected from the group consisting of the sequences set forth as SEQ ID NOS: 16, 19, 20, 23, and 24.

18. The method of claim 2, wherein the sequence of the at least one antisense oligonucleotide comprises a sequence selected from the group consisting of the sequences set forth as SEQ ID NOS: 16-31 and 35.

19. The method of claim 18, wherein the sequence of the at least one antisense oligonucleotide comprises a sequence selected from the group consisting of the sequences set forth as SEQ ID NOS: 16, 19, 20, 23, and 24.

20. The method of claim 3, wherein the sequence of the at least one antisense oligonucleotide comprises a sequence selected from the group consisting of the sequences set forth as SEQ ID NOS: 16-31 and 35.

21. The method of claim 20, wherein the sequence of the at least one antisense oligonucleotide comprises a sequence selected from the group consisting of the sequences set forth as SEQ ID NOS: 16, 19, 20, 23, and 24.

22. A method of upregulating the expression of a Brain derived neurotrophic factor (BDNF) polynucleotide in a biological system comprising: contacting the system with at least one antisense oligonucleotide 10 to 30 nucleotides in length wherein the at least one antisense oligonucleotide is at least 90% complementary to and specifically hybridizes to a 10 to 30 nucleotide region of a 225-nucleotide overlapping region of a natural antisense polynucleotide of the BDNF polynucleotide, wherein the 225-nucleotide overlapping region of the natural antisense polynucleotide has at least 95% complementarity to the 225-nucleotide region at nucleotides 1188 to 1412 of the BDNF mRNA of SEQ ID NO: 1, thereby upregulating the expression of the BDNF polynucleotide.

23. The method of claim 22, wherein the 225-nucleotide overlapping region of the natural antisense polynucleotide has 100% complementarity to nucleotides 1188 to 1412 of the BDNF mRNA of SEQ ID NO: 1.

* * * * *

UNITED STATES PATENT AND TRADEMARK OFFICE
CERTIFICATE OF CORRECTION

Page 1 of 1

PATENT NO. : 10,214,745 B2
APPLICATION NO. : 15/398630
DATED : February 26, 2019
INVENTOR(S) : Mohammad Ali Faghihi et al.

It is certified that error appears in the above-identified patent and that said Letters Patent is hereby corrected as shown below:

In the Specification

Column 1, after Line 16, please insert the following heading and paragraph:
--STATEMENT AS TO FEDERALLY SPONSORED RESEARCH
This invention was made with the support of the United States government under grant numbers 5R01NS063974-02 awarded by the National Institute of Neurological Disorders and Stroke and 5RC2AG036596-02 awarded by the National Institute on Aging. The government has certain rights in this invention.--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*